(12) United States Patent
Kim et al.

(10) Patent No.: US 8,889,345 B2
(45) Date of Patent: Nov. 18, 2014

(54) DETECTION METHODS OF NADP(H) USING MBFP

(71) Applicant: Industry Foundation of Chonnam National University, Gwangju (KR)

(72) Inventors: Geun Joong Kim, Gwangju (KR); Sung Hwan You, Gwangju (KR)

(73) Assignee: Industry Foundation of Chonnam National University, Gwangju (KR)

( * ) Notice: Subject to any disclaimer, the term of this patent is extended or adjusted under 35 U.S.C. 154(b) by 116 days.

(21) Appl. No.: 13/811,809

(22) PCT Filed: Dec. 24, 2012

(86) PCT No.: PCT/KR2012/011334
§ 371 (c)(1),
(2), (4) Date: Jan. 23, 2013

(87) PCT Pub. No.: WO2014/038758
PCT Pub. Date: Mar. 13, 2014

(65) Prior Publication Data
US 2014/0273011 A1    Sep. 18, 2014

(30) Foreign Application Priority Data

Sep. 4, 2012 (KR) .................. 10-2012-0097507

(51) Int. Cl.
*C12Q 1/00* (2006.01)
*G01N 33/53* (2006.01)
*C07K 1/00* (2006.01)
*G01N 33/573* (2006.01)

(52) U.S. Cl.
CPC ............................ *G01N 33/5735* (2013.01)
USPC ........................... 435/4; 435/7.72; 530/350

(58) Field of Classification Search
None
See application file for complete search history.

(56) References Cited

U.S. PATENT DOCUMENTS 8,552,151 B2 * 10/2013 Chang .......................... 530/350

* cited by examiner

*Primary Examiner* — Suzanne M Noakes
*Assistant Examiner* — Jae E Lee
(74) *Attorney, Agent, or Firm* — Sughrue Mion, PLLC

(57) ABSTRACT

Provided is a detection method of NADP(H) from the change of a fluorescence intensity by a reaction between metagenome-derived blue fluorescent protein (mBFP) and NADPH. More particularly, the present invention relates to methods for detecting NADP(H) using mBFP or his-mBFP, or methods for detecting NADP(H) for measuring an activity of NADP (H) dependent dehydrogenase or oxidoreductase.

6 Claims, 14 Drawing Sheets

Figure 1

A   Base sequence of mBFP

1    ATGCAGAATC TGAACGGCAA AGTGGCTTTC GTGACCGGCA GCAGCCGCGG
51   CATCGGCGCG GCGATCGTCC GCGCTTGGC GGCGGACGGC GCCGACATCG
101  CGTTCACCTA TGTCAGCGC TGTCGAAAA ACTGGCCAC CGCCCTGGTG
151  CAAGAACTCG AGGCCAAGCG GGCGGCCGCT CGCGCATCC AGGCGGACTC
201  GGCGGATCCG GCGCAGGTCG GCAGCGGT CGACAGGCC ATCGTGCAAC
251  TGGGCCCGGT GGACGTGCTG GTGAACAACG CCGGCATCTT CCTGGCCGGC
301  CCCTTGGCG AGGTGACGCT GGACGACTAC GAACGCACGA TGAACATCAA
351  TGTGCGCGC CCTTCGTG CACCCAGGC CGGCAAGCC TCGATGCCGG
401  ACGCGGCCG GATCATCAAC ATCGGCAGCT GCTGGCGGA ACGGCCGGC
451  CGAGCCGGG TAACGCTGTA TGCCGCCAGC AAGTCGGCGC TGCTGGGCAT
501  GACGCGCGC CTGGCGGCG ACCTGGCGCT GCATGGCATC ACCGCCAACG
551  TCGTGCACCC GGGTCCATC GACACCGACA TGAATCCCGG AGATGCGGAA
601  CGCTGGGCA AACTGGCGGC CGTGCTGTCC TTCCTCATT ACGGCGAGCT
651  GCGGCACATC GCCGGCATGG TGGCTTGCCT GGTCGGCCGA GATGGCGCT
701  ACGTGACCGG TGCGAGTCTG GCGGTGGACG GCGGCTTCGC CGCTTGA

B   Amino acid sequence of mBFP

1    MQNLNGKVAF VTGGSRGIGA AIVRELAADG ADIAFTYVSA GSNVATALV
QELEAKGRAA
61   RAIQADSADF AQVRQAVEQA IVQLGPVDVL VNNAGIFLAG PLGEVTLDDY
ERTMNINVRA
121  FFAIQAQA SMPDGSKIN IGSCLAERAS SAGVTLAAS KSALLGMTRG
LARIGAGSI
181  TNVYHSFI DTDMNPADGE RSGLVAVLS LFHIGEVRSI AGVYAKLASP
DGRYVTGASL
241  AVDGGFAA

Figure 2

A   Base sequence of His-mBFP

1    ATGAGAGGAT CGCATCACCA TCACCATCAC GGATCCGCAT GCCAGAATCC
51   GAACTGCAAA ATGGCTTTCG TGACCGGCAG CAGCCGTGGC ATCGGTGCGG
101  CGATCGTCCG CCGCTGGCG GCGGACGGCG CCGACATCGC GTTCACCTAT
151  GTCAGCGCT CGTGGAAAA CGTGCCACC GCCTGGTGC AAGAACTCGA
201  GGCCAAGGC DGCCGGCTC GCGCCATCCA GGCGGATCG GCGGATCGG
251  CCCAGGTCG GCAAGCGGTC GAGCAGGCCA TCGTGCAACT GGGGCCGGTG
301  GACGTGCTGG TGAACGACGC CGGCATCTTC CTGGCCGGCC CCTGGGCGA
351  GGTGACCCTG GACGACTACG AACGCACCAT GAACATCAAT GTCCGCGCCC
401  CTTCGGGC CATCCAGGCC GCGCAGGCCT CGAGCCCGA CGGCGGCCGC
451  ATCATCAACA TCGGCAGCTG CCTGGCCGAA CGCGCCGGCC GAGCCGGGGT
501  AACGCTGTAT GCCGCCAGCA AGTCGGCGCT GCTGGGCATG ACGCGCGACC
551  TGCGCGCGA CCTGGCCGCG CGCGGCATCA CCGCCAACGT CGTGCACCCG
601  GGCCCGATCG ACACCGACAT GAATCCCGCA GATGGCGAAC GCTCGGCGA
651  ACTGGTGGCC GTGCTGTCCT TGCCTCATTA CGGCGAGGTG CGCGACATCG
701  CCGGCATGGT GGCTTCCCTG GCCGGCCGG ATGGGCGCTA CGTGACCGGT
751  GCGAGTCTGG CGGTGGACGG CGGCTTCGCC GCTTGA

B   Amino acid sequence of His-mBFP

1    MRGSHHHHHH GSADQNLNGF VAFVTGSSRG IGKAIVRRLA ADGADIAFTY
51   VSASRNVAT ADVGELSAKD RRARA DQADS AGPAQVEQAV SQRIVQLGPV
101  DVLVNNAGIF LAGPLGEVTL DDYERTMNIN VRAPFVAIQA AQASNPDGGS
151  IINIGSCLAE RAGRASVTLY AASKSALLGM TRLARDLGA AGITANVVHP
201  GPIDTDMNPA DGERSGELVA VLSLPHYGEV RDIAGMVASL AGPDGRYVTG
251  ASLAVDGGFA A

E. coli exhibiting fluorescence due to increased physiological
activity caused by using contamination organic materials
as nutrients

SEQUENCE LISTING

<160> NUMBER OF SEQ ID NOS: 6

<210> SEQ ID NO 1
<211> LENGTH: 248
<212> TYPE: PRT
<213> ORGANISM: artificial

```
<220> FEATURE:
<223> OTHER INFORMATION: synthetic construct of metagenome-derived blue
      fluorescent protein (mBFP)

<400> SEQUENCE: 1

Met Gln Asn Leu Asn Gly Lys Val Ala Phe Val Thr Gly Gly Ser Arg
1               5                   10                  15

Gly Ile Gly Ala Ala Ile Val Arg Arg Leu Ala Ala Asp Gly Ala Asp
                20                  25                  30

Ile Ala Phe Thr Tyr Val Ser Ala Ser Ser Lys Asn Val Ala Thr Ala
            35                  40                  45

Leu Val Gln Glu Leu Glu Ala Lys Gly Arg Arg Ala Arg Ala Ile Gln
50                  55                  60

Ala Asp Ser Ala Asp Pro Ala Gln Val Arg Gln Ala Val Glu Gln Ala
65                  70                  75                  80

Ile Val Gln Leu Gly Pro Val Asp Val Leu Val Asn Asn Ala Gly Ile
                85                  90                  95

Phe Leu Ala Gly Pro Leu Gly Glu Val Thr Leu Asp Asp Tyr Glu Arg
            100                 105                 110

Thr Met Asn Ile Asn Val Arg Ala Pro Phe Val Ala Ile Gln Ala Ala
        115                 120                 125

Gln Ala Ser Met Pro Asp Gly Gly Arg Ile Ile Asn Ile Gly Ser Cys
130                 135                 140

Leu Ala Glu Arg Ala Gly Arg Ala Gly Val Thr Leu Tyr Ala Ala Ser
145                 150                 155                 160

Lys Ser Ala Leu Leu Gly Met Thr Arg Gly Leu Ala Arg Asp Leu Gly
                165                 170                 175

Ala Arg Gly Ile Thr Ala Asn Val Val His Pro Gly Pro Ile Asp Thr
            180                 185                 190

Asp Met Asn Pro Ala Asp Gly Glu Arg Ser Gly Glu Leu Val Ala Val
        195                 200                 205

Leu Ser Leu Pro His Tyr Gly Glu Val Arg Asp Ile Ala Gly Met Val
210                 215                 220

Ala Phe Leu Ala Gly Pro Asp Gly Arg Tyr Val Thr Gly Ala Ser Leu
225                 230                 235                 240

Ala Val Asp Gly Gly Phe Ala Ala
                245

<210> SEQ ID NO 2
<211> LENGTH: 747
<212> TYPE: DNA
<213> ORGANISM: artificial
<220> FEATURE:
<223> OTHER INFORMATION: synthetic construct of metagenome-derived blue
      fluorescent protein (mBFP)

<400> SEQUENCE: 2
atgcagaatc tgaacggcaa agtggctttc gtgaccggcg gcagccgcgg catcggcgcg      60
gcgatcgtcc gccgcttggc ggcggacggc gccgacatcg cgttcaccta tgtcagcgcc     120
tcgtcgaaaa acgtggccac cgccctggtg caagaactcg aggccaaggg ccgccgcgct     180
cgcgccatcc aggcggactc ggcggatccg gcccaggtgc ggcaggcggt cgagcaggcc     240
atcgtgcaac tggggccggt ggacgtgctg gtgaacaacg ccggcatctt cctggccggc     300
cccttgggcg aggtgacgct ggacgactac gaacgcacga tgaacatcaa tgtgcgcgcg     360 ccttcgtgg ccatccaggc cgcgcaggcc tcgatgccgg acggcggccg catcatcaac     420
```

```
atcggcagct gcctggcgga acgcgccggc cgagccgggg taacgctgta tgccgccagc    480
aagtcggcgc tgctgggcat gacgcgcggc ctggcgcgcg acctgggcgc gcgcggcatc    540
accgccaacg tcgtgcaccc gggcccgatc gacaccgaca tgaatcccgc agatggcgaa    600
cgctcgggcg aactggtggc cgtgctgtcc ttgcctcatt acggcgaggt gcgcgacatc    660
gccggcatgg tggctttcct ggccgggccg gatgggcgct acgtgaccgg tgcgagtctg    720
gcggtggacg gcggcttcgc cgcttga                                        747
```

```
<210> SEQ ID NO 3
<211> LENGTH: 261
<212> TYPE: PRT
<213> ORGANISM: artificial
<220> FEATURE:
<223> OTHER INFORMATION: synthetic construct of His-tagged
      metagenome-derived blue fluorescent protein (mBFP)
<220> FEATURE:
<221> NAME/KEY: MISC_FEATURE
<222> LOCATION: (5)..(10)
<223> OTHER INFORMATION: histine tag

<400> SEQUENCE: 3

Met Arg Gly Ser His His His His His His Gly Ser Ala Cys Gln Asn
1               5                   10                  15

Leu Asn Gly Lys Val Ala Phe Val Thr Gly Gly Ser Arg Gly Ile Gly
            20                  25                  30

Ala Ala Ile Val Arg Arg Leu Ala Asp Gly Ala Asp Ile Ala Phe
        35                  40                  45

Thr Tyr Val Ser Ala Ser Ser Lys Asn Val Ala Thr Ala Leu Val Gln
50                  55                  60

Glu Leu Glu Ala Lys Gly Arg Arg Ala Arg Ala Ile Gln Ala Asp Ser
65                  70                  75                  80

Ala Asp Pro Ala Gln Val Arg Gln Ala Val Glu Gln Ala Ile Val Gln
                85                  90                  95

Leu Gly Pro Val Asp Val Leu Val Asn Asn Ala Gly Ile Phe Leu Ala
            100                 105                 110

Gly Pro Leu Gly Glu Val Thr Leu Asp Asp Tyr Glu Arg Thr Met Asn
        115                 120                 125

Ile Asn Val Arg Ala Pro Phe Val Ala Ile Gln Ala Ala Gln Ala Ser
130                 135                 140

Met Pro Asp Gly Gly Arg Ile Ile Asn Ile Gly Ser Cys Leu Ala Glu
145                 150                 155                 160

Arg Ala Gly Arg Ala Gly Val Thr Leu Tyr Ala Ala Ser Lys Ser Ala
                165                 170                 175

Leu Leu Gly Met Thr Arg Gly Leu Ala Arg Asp Leu Gly Ala Arg Gly
            180                 185                 190

Ile Thr Ala Asn Val Val His Pro Gly Pro Ile Asp Thr Asp Met Asn
        195                 200                 205

Pro Ala Asp Gly Glu Arg Ser Gly Glu Leu Val Ala Val Leu Ser Leu
210                 215                 220

Pro His Tyr Gly Glu Val Arg Asp Ile Ala Gly Met Val Ala Phe Leu
225                 230                 235                 240

Ala Gly Pro Asp Gly Arg Tyr Val Thr Gly Ala Ser Leu Ala Val Asp
                245                 250                 255

Gly Gly Phe Ala Ala
            260
```

```
<210> SEQ ID NO 4
<211> LENGTH: 786
<212> TYPE: DNA
<213> ORGANISM: artificial
<220> FEATURE:
<223> OTHER INFORMATION: synthetic construct of His-tagged
      metagenome-derived blue fluorescent protein (mBFP)

<400> SEQUENCE: 4
atgagaggat cgcatcacca tcaccatcac ggatccgcat gccagaatct gaacggcaaa      60
gtggctttcg tgaccggcgg cagccgcggc atcggcgcgg cgatcgtccg ccgcttggcg     120
gcggacggcg ccgacatcgc gttcacctat gtcagcgcct cgtcgaaaaa cgtggccacc     180
gccctggtgc aagaactcga ggccaagggc cgccgcgctc gcgccatcca ggcggactcg     240
gcggatccgg cccaggtgcg gcaggcggtc gagcaggcca tcgtgcaact ggggccggtg     300
gacgtgctgg tgaacaacgc cggcatcttc ctggccggcc ccttgggcga ggtgacgctg     360
gacgactacg aacgcacgat gaacatcaat gtgcgcgcgc ctttcgtggc catccaggcc     420
gcgcaggcct cgatgccgga cggcggccgc atcatcaaca tcggcagctg cctggcggaa     480
cgcgccggcc gagccggggt aacgctgtat gccgccagca agtcggcgct gctgggcatg     540
acgcgcggcc tggcgcgcga cctggcgcg cgcggcatca ccgccaacgt cgtgcacccg     600
ggcccgatcg acaccgacat gaatcccgca gatggcgaac gctcgggcga actggtggcc     660
gtgctgtcct tgcctcatta cggcgaggtg cgcgacatcg ccggcatggt ggctttcctg     720
gccgggccgg atgggcgcta cgtgaccggt gcgagtctgg cggtggacgg cggcttcgcc     780
gcttga                                                                786

<210> SEQ ID NO 5
<211> LENGTH: 22
<212> TYPE: DNA
<213> ORGANISM: artificial
<220> FEATURE:
<223> OTHER INFORMATION: primer

<400> SEQUENCE: 5
atagcatgcc agaatctgaa cg                                               22

<210> SEQ ID NO 6
<211> LENGTH: 25
<212> TYPE: DNA
<213> ORGANISM: arificial
<220> FEATURE:
<223> OTHER INFORMATION: primer

<400> SEQUENCE: 6
ataaagcttt caagcggcga agccg                                            25
```

DETECTION METHODS OF NADP(H) USING MBFP

CROSS REFERENCE TO RELATED APPLICATIONS

This application is a National Stage of International Application No. PCT/KR/2012/011334, filed on Dec. 24, 2012, which claims priority form Korean Patent Application No. 10-2012-0097507, filed Sep. 4, 2012, the contents of all of which are incorporated herein by reference in their entirety.

TECHNICAL FIELD

The present invention relates to a detection method of NADP(H) from the change of a fluorescence intensity by a reaction between metagenome-derived blue fluorescent protein (mBFP) and NADPH, and more particularly, to a detection method of NADP(H) using mBFP or his-mBFP, or a detection method of NADP(H) for measuring an activity of NADP(H) dependent dehydrogenase or oxidoreductase.

BACKGROUND ART

Nicotinamide adenine dinucleotide phosphate (reduced form, NADPH) is a kind of coenzyme participating in reactions of a lot of oxidoreductase and dehydrogenase as an electron donor to provide reducing power together with NADH sharing a nicotinamide adenine dinucleotide structure. Oxides (NAD+ and NADP+) of these coenzymes perform an important function of receiving energy generated in biological catabolism in the form of electron and proton and participate in the reaction of oxidoreductase as an electron acceptor.

As well known, a main metabolism of a biological system is configured of a generation process of main precursors and energy by oxidation (catabolism) of nutrients inputted from the outside and a synthesis process (anabolism, which is mainly reduction reaction) of bio-molecules using the generated precursors and energy. A form of bio-energy generated in the oxidation (catabolism) process and consumed in the synthesis (anabolism) process is the electron and the proton, and the main carriers of these compounds are NADP(H) and NAD(H). The reason that two kinds of biological coenzymes capable of mediating chemically the same reaction exist is known as evolutional selection for appropriately distributing oxidizing (or reducing) power required for the catabolism and reducing (or oxidizing) power required for the anabolism and efficiently adjusting a flow of energy.

Therefore, it is known that since catabolism is mainly the oxidation reaction, and anabolism is mainly the reduction reaction, a molar ratio of NADPH is relatively higher than that of NADP+ in vivo and a molar ratio of NAD+ is relatively higher than that of NADH. In addition, in the metabolism/energy related processes in organisms growing through anaerobic respiration or fermentation and most of the organisms using an inorganic substance as an energy donor as well as in a respiration process in a general oxygen dependent cell using oxygen as a final electron acceptor, a coenzyme used as a high energy intermediate compound or an electron acceptor/donor is NADP(H) or NAD(H).

It is known that since it is very important to maintain a balance between these coenzymes due to specialized functions of the two kinds of coenzymes (NADP(H) or NAD(H)) in vivo, a salvage pathway (a pathway in which reduced NADPH reduces NAD+ or a reverse pathway thereof) capable of inducing an oxidized/reduced form of each other is present between the NADP(H) and NAD(H).

Therefore, a ratio of oxidized/reduced coenzyme is used as a very important biological activity marker in all of the cells in the ecosystem. That is, whether or not the cell maintains a normal biological activity and a difference in the biological activity may be prescribed by a method of quantifying a concentration of these coenzymes in vivo. As described above, it is known that in the case in which an accurate detection method for any one of the two kinds of coenzymes is present, concentrations of these coenzymes or a content of each of the oxidized/reduced form thereof may be quantified due to biochemical association between these coenzymes.

That is, as the function of these coenzymes in vivo, in the case of NAD(H), NAD(H) plays a very important role in energy generation or energy storage in a glycolytic process, which is a first process of the central metabolism in living organisms, a pentose phosphate pathway, and a TCA cycle. In the case of NADP(H), it is known that since NADP(H) is used to synthesize important biopolymers such as fatty acids, amino acids, and nucleic acids, the NADP(H) may be an important marker to activity measurement of various cells in a human body and as well as the physiological activity, presence or absence of metabolic disorders according to activity ratios thereof, analogy of a carcinogenesis process, a probe, or the like. In the case of living cells, since a relative difference in the concentration of these coenzymes in vivo or a ratio of oxidation/reduction is clear and is an absolute factor in the physiological activity, the coenzymes may also be a useful marker in determining a presence or absence of a cell in a specific sample (water quality analysis or confirmation of food contaminations) or a degree of the cell (possibility of causing a disease).

Therefore, a measuring method for accurate quantities of the two kinds of coenzymes may be widely used in various fields, such that various researches into the development of a measuring method of the coenzymes have been conducted, and various methods has been attempted in order to develop methods for detecting NADP(H) which has a relatively excellent optical property and of which a compound itself has a fluorescence intensity of a predetermined level. As described above, the accurate detection method of NADP(H) may provide an indirect detection method for oxidized NADP+, NADH or NAD+ by the coupling of salvage enzymes in addition to being used to measure NADPH itself.

A general method used for detection of NADPH, which is a main biological activity marker, is a method of measuring absorbance using a natural wavelength of NADPH itself or measuring fluorescence. The method of measuring absorbance is a method of measuring a light absorption degree at a wavelength of 340 to 345 nm, which is the intrinsic wavelength, using a UV spectrophotometer and then determining a quantity using a standard curve. In the case of the method for measuring the fluorescence, a method of irradiating light at about 350 nm at which maximum fluorescence appears through excitation scanning, and then measuring relative value at an emission wavelength (about 450 nm) to determining an amount corresponding thereto in a standard curve may be used.

The above-mentioned analysis methods have an advantage in that since addition of a separate substrate is not required, the measurement may be relatively simple, but have a disadvantage in that since the absorbance and fluorescence value of NADPH itself are low, a relatively accurate value may be measured in only pure reactant composition (including only a buffer and the coenzyme). Basically, since molecular extinction coefficient or quantum yield is low, the analysis method has a significant disadvantage in that a relatively large amount of samples of a predetermined level or more has been required.

The problem means that it is difficult to directly use the method in various biological or environmental samples unlike an artificial experimental sample in which an accurate composition ratio of the composition is known. The reason is that substance absorbing light or fluorescing at these wavelengths that are known as the intrinsic property of NADPH or various chemicals in environment may cause interference. Therefore, an S/N ratio (signal/noise ratio) may be frequently reduced, and sensitivity may be reduced, such that the measurement may be performed only in the case in which a concentration of NADPH in the sample is relatively high.

Another disadvantage of the current used method is that in the case in which a small amount of coenzyme exists, a measurement time may be delayed due to a complicated pre-treatment process generally used in order to solve a problem of NADPH having a low optical property. As described above, in the case in which an amount of coenzymes to be measured is small, the pre-treatment process for removing interference factors affecting the signal/noise ratio in vivo and in vitro is essential. This pre-treatment process includes steps such as a step of centrifugation, a step of inducing aggregation of the interference substances, or a step of concentration, and a time required to perform the pre-treatment process is 30 minutes to several hours (3 to 4 hours) according to the used process.

Through the process, interference may be partially reduced, and NADPH may be concentrated, but natural oxidation of NADPH according to the pre-treatment time may cause another problem. As well known, since NADPH having strong reducing power may easily provide the reducing power to other substances, NADPH has a chemical property in that it may be easily oxidized when it is exposed to air.

Therefore, there is a problem in that as the pre-treatment time become long, NADPH is converted into NADP+, which is relatively difficult to be measured, due to the natural oxidation by air, instability according to pH of the buffer, and reaction results with oxides in the reaction solution. Therefore, addition of a reagent suppressing oxidation of NADPH or inducing structural stability is separately required.

As a partial complementary measure of these problems, many kits currently sold in the market use the principle of coupling reaction in which cyclase for inducing reduction of the oxidized coenzyme (NADP+) or various dehydrogenases inducing reduction of NADP+ to NADPH through an oxidation reaction of a specific substrate using NADP+ as a coenzyme are included. However, there are disadvantages in that the enzyme source used in these reactions is expensive, stability is low, and another substrate should be added for measurement of the coenzyme.

Particularly, in the case of cyclase, ATP, which is another expensive coenzyme, should be necessarily added. As expected, during the process, since oxidized NADP+ already existing in the sample is also reduced and measured, a total amount of NADP+/NADPH is measured, instead of an absolute amount of NADPH in the sample or a relative ratio of the NADPH to the oxidized coenzyme.

In the kit sold on the market, as a complementary measure of low absorbance (fluorescence) property of NADPH, a method of inducing conversion of a specific fluorescent substrate using NADPH as a coenzyme and measuring fluorescence of a specific product increased accordingly may be used. In the above mentioned method, there is an advantage in that NADPH itself having low sensitivity that is difficult to be measured may be detected at a relatively high sensitivity using an artificial substrate having a high quantum yield, but there is a disadvantage in that enzyme to be coupled is required and an expensive artificial fluorescent substrate should be used, such that there are many limitations in using the method.

DISCLOSURE

Technical Problem

While conducting continuous studies in order to solve these problems, the present inventors discovered a novel detection of NADP(H) capable of being rapidly performed without complicated pre-treatment and addition of a substrate and having high accuracy and sensitivity even under oxygen-free condition to thereby be conveniently used by only adding a specific protein having an amino acid sequence of SEQ ID NO: 1 to a reaction solution extracted from a sample, unlike the existing detection system for NADPH that requires enzymes such as oxidoreductase or cyclase and a substrate, thereby completing the present invention.

An object of present invention is to provide a detection method for NADP(H) capable of being rapidly performed without complicated pre-treatment and having high accuracy and sensitivity even under the oxygen-free condition by using a novel protein directly bound to the coenzyme to increase fluorescence, that is, his-metagenome-derived blue fluorescent protein (his-mBFP), or methods for detecting NADP(H) for measuring an activity of NADP(H) dependent enzyme.

Another object of the present invention is to provide a measuring method for a physiological/biological activity in various fields by fusing with an additional method and a recovering method for NADPH using a coupling force of mBFP or his-mBFP to NADPH, as an application of the detection method of NADP(H).

In order to achieve these objects, the present inventors discovered a novel detection method of NADP(H) or NADP (H) dependent enzymes capable of increasing fluorescence intensity of NADPH from 7 to 20 times to have excellent measuring capacity by adding a metagenome-derived blue fluorescent protein (mBFP) to a reaction solution extracted from a sample, thereby completing the present invention.

Technical Solution

In one general aspect, the present invention is to provide a detection method of NADP(H) from the change of a fluorescence intensity by a reaction between metagenome-derived blue fluorescent protein (mBFP) and NADPH.

The mBFP may have an amino acid sequence of SEQ ID NO: 1 and further include an affinity tag, preferably histidine-tag (his-tag). The his-mMBF may have an amino acid sequence of SEQ ID NO: 3. A concentration of NADP(H) existing in a sample may be measured from the change in fluorescence due to reaction between mBFP and NADPH.

In another general aspect, there is provided a method of measuring an activity of a NADP(H) dependent enzyme using NADP(H) as a coenzyme, preferably, a NADP(H) dependent dehydrogenase or oxidoreductase through a change in fluorescence caused by a reaction between mBFP and NADPH.

At the time of the reaction of sample and mBFP, a detergent, preferably, at least one kind selected among sodium dodecylsulfate (SDS), Na-deoxycholate, cetyltrimethylammonium bromide (CTAB), dodecylethyldimethyl-ammonium bromide (DEDAB), and 3-[(3-cholamidopropyl)dimethylammonio]-1-propane sulfonate (CHAPS) may be added and mixed.

In another general aspect, there is provided a NADPH detection kit including a c. The mBFP may further include a histidine tag (his-tag). The his-mBFP may have an amino acid sequence of SEQ ID NO: 3.

The NADPH kit may further include a detergent, a reducing agent, and a washing solution. And the kit may be used for recovering the NADPH and NADPH may be recovered using affinity chromatography from the kit.

The detection method according to an exemplary embodiment of the present invention includes methods for measuring the activities of NADP(H) dependent enzymes from fluorescence intensity, a test method capable of efficiently selecting a NADP(H) dependent oxidoreductase inhibitor (anti-microbial agent).

The fluorescent change according to the exemplary embodiment of the present invention is characterized in that mBFP is directly bound to NADPH present in the sample to increase or decrease the fluorescence intensity, and then a concentration of NADP(H) or an activity of NADP(H) dependent oxidoreductase are measured based on the increased or decreased fluorescence intensity. See FIG. 3.

In the detection method according to the exemplary embodiment of the present invention, since mBFP is directly bound to NADPH present in living organism/environment without a complicated pre-treatment and addition of a substrate to increase the fluorescence intensity, dependence on physical/chemical reaction variables may be reduced, and the fluorescence intensity may be in proportion to the concentration of NADPH.

In the detection method according to the exemplary embodiment of the present invention, a time required to form a fluorophore may be significantly short, and the method may be independent of oxygen unlike other fluorescent protein or other enzymes coupled to the existing NADPH assay kit to induce luminescence to generate fluorescence. Therefore the method of the present invention can detect NADP(H) in almost real time (that is, on-line monitoring may be performed) and have excellent accuracy and high sensitivity.

The mBFP according to the exemplary embodiment of the present invention has the amino acid sequence of SEQ ID NO: 1, wherein in consideration of degeneracy of a gene code and conservative substitution of amino acid, a protein having a homology of 80%, preferably 85%, more preferably 90%, most preferably 95% with the sequence of SEQ ID NO: 1 may be included in mBFP protein according to the present invention.

The mBFP according to the exemplary embodiment of the present invention may further include an affinity tag, wherein as the affinity tag, a histidine tag (his-tag) may be used.

The mBFP according to the exemplary embodiment of the present invention further includes the affinity tag, such that a large amount of his-mBFP may be recovered with high purity in a single process.

The mBFP including the affinity tag according to the exemplary embodiment of the present invention may have an amino sequence shown in a sequence number 3. See FIGS. 2A and 2B.

More specifically, for large scale separation and purification of mBFP with high purity, a poly histidine tag capable of using affinity chromatography was attached to the mBFP. Generally, in a purification process of protein, a method of performing a density gradient centrifugation, salting out, or dialysis, performing an ion-exchange or gel filtration chromatography in multi-steps, and then concentrating the protein is mainly used. During this process, purity of the protein may be increased, but yield may be significantly decreased. In purification of protein in which it is difficult to use this method, a method of using a column using a hydrophobic interaction or a method of directly eluting the protein from a gel after electrophoresis may be used.

Since the mBFP including the affinity tag according to the exemplary embodiment of the present invention may be naturally bound to NADPH, a cibacron blue based affinity column may be used, but in the present invention, in consideration of binding force and yield, high purity/large scale purification and detection method were established by integrating the polyhistidine tag. According to this strategy, purification of protein may be performed in a single process, and in some cases, two affinity columns (cibacron blue and Ni-NTA) may be continuously used in order to remove impurities. To this end, his-mBFP was prepared by a method of inserting the mBFP gene into a pQE30 plasmid mounted with the his-tag or preparing the mBFP gene including the his-tag at an N-terminal thereof to transform a host cell. Over-expressed his-mBFP was separated and purified form the host cell transformed by the prepared gene using Ni-NTA, which is the affinity chromatography. See FIGS. 4 and 5.

In the case of the separated and purified his-mBFP, it was confirmed that the his-mBFP has the same NADPH dependent fluorescence intensity as that of wild-type protein, such that the his-tag fused with the N-terminal has no influence on the optical property. See FIG. 6.

The present invention provides a method of directly or indirectly detecting NADP(H) in biological/environmental samples using the purified his-mBFP using the affinity tag and, especially optimum reaction conditions for measuring activities of various enzymes using NADPH as a coenzyme.

First, dependency of mBFP according to a reaction temperature was confirmed. That is, when a fluorescence value of mBFP by binding NADPH according to a change in a temperature was measured, and as a result, it was confirmed that linear reaction characteristics were shown in various temperature sections and a difference in maximum fluorescence values according to the temperature was not large. This property shows that the detection method may be used in all of the temperature ranges as long as protein itself is not deformed.

Therefore, his-mBFP according to the present invention may be used at a low temperature at which it is difficult to use the existing NADPH assay kit since the activity of a general enzyme is significantly reduced, as well as in a temperature range in which coupling enzyme of the existing NADPH assay kit has the activity. In addition, under the condition described above, since the natural oxidation of NADPH is small, the present invention has an advantage in that there is no need for an oxidation inhibitor or a fixing agent.

Second, fluorescence variations and intensity of mBFP according to a pH of the buffer were analyzed, and whether the problem of limitation in the buffer according to the existing method may be solved was confirmed. As a result, blue fluorescence dependent on the concentration of NADPH was confirmed under a buffer condition from a weak acid buffer (pH: 5.0) to a basic buffer (pH: 10.0). Therefore, it was confirmed that the detection method according to the present invention may be used under most of the conditions except for strong acid and strong base buffer capable of causing deformation of protein.

The above-mentioned property is an advantage of the detection method requiring only simple binding of NADPH, and it is confirmed that when considering pH of the buffer and a salt concentration exhibiting the linear reaction characteristics, most of the samples in a natural ecosystem as well as most of the biological samples having a near-neutral pH and salt concentration may be used in assays by only simple pre-treatment process such as a dilution process.

Third, fluorescence of mBFP according to a reaction time of mBFP and NADPH was investigated.

More specifically, in order to confirm a time required to increase fluorescence according to the addition of NADPH to the his-mBFP reaction solution, the fluorescence lifetime was measured while a reaction time is changed in a state in which a temperature was fixed at 30° C.

As a result, it was confirmed that the fluorescence is increased immediately after addition of NADPH. It was confirmed that the fluorescence intensity approaches at the maximum value in the reaction time of 1 to 5 minutes and is dependent on the concentration of NADPH. This result means that in the case of mixing a reaction composition in an equilibrium state at a desired temperature, the concentration of NADPH may be reproducibly measured about 1 minute.

Therefore, it may be re-confirmed that in the case of using his-mBFP according to the present invention, since NADPH may be measured in a wide concentration range (10 nM to 15 µM) within a short time (1 to 5 minutes), there is no need for treatment of NADPH oxidation inhibitor or addition of the fixing agent.

In addition, it means that the problem that a time required to induce reaction of the coupled dehydrogenase in the existing NADPH assay kit is at least 30 minutes and the other problems that the NADPH cannot be measured over a wide concentration range, are now completely solved by the present invention. Therefore, with the detection method according to the present invention, in a screening process of useful enzymes such as NADPH-dependent oxidoreductase present in various biological/environmental samples, after his-mBFP is added to the sample, the related enzyme sources may be selected in real time.

Fourth, the optimum concentration of mBFP or his-mBFP at which a concentration of NADPH present in various biological/ecological samples may be accurately, rapidly, and economically measured was investigated. More specifically, in order to confirm fluorescence intensity according to the concentration of mBFP or his-mBFP and a linear range, the concentration of NADPH was measured while the concentration of mBFP is changed.

As a result, it was confirmed that the concentration of NADPH may be reproducibly measured at an mBFP concentration of 1 µM or more. It was confirmed that this property may be implemented at a protein concentration of 10 µM, wherein the measurable concentration range of NADPH is 10 nM to 1 mM. It may be re-confirmed through this measuring range that the measuring method according to the present invention has similar to or higher sensitivity as compared to the existing kit and is a relatively advantageous measuring method when considering a time required for measurement or the pre-treatment process.

The result may be caused by a feature that each of the mBFP monomer having a tetramer structure as a quaternary structure may be bound to a single NADPH. Since four monomers bound to NADPH exhibit increased fluorescence, theoretically a mole ratio required for measurement is 4:1 (NADPH:mBFP). Therefore, 1 µM of optimized mBFP may be bound to 4 µM of NADPH. Comparably, the existing kits using oxidoreductase or cyclase having a catalytic function as a coupled protein requires a relatively large amount of proteins. The reason is that diffusion by a concentration difference and collision are very important factors in a catalytic activity and oxidoreductase or cyclase have a relatively low affinity with NADPH.

In addition to the above-mentioned advantages, since his-mBFP is over-expressed in $E.\ coli$ at a content of 25% or more based on the total protein content, assay may be performed 80 to 800 times using 80 mg of protein obtained from a typical culture medium (LB+50 mg/ml of ampicillin) in a single process, such that it may be confirmed that the method according to the present invention is an economically advantageous method. Particularly, the present invention has another advantage that expensive IPTG as an inducer of expression of his-mBFP is not required, such that manufacturing cost of protein may be cheap, unlike alkaline phosphatase and luciferase coupled to the existing kit.

In the detection method according to the exemplary embodiment of the present invention, a detergent may be further added and mixed at the time of reaction of the sample and his-mBFP.

The detergent according to the exemplary embodiment of the present invention may be at least one kind selected from SDS, Na-deoxycholate, CTAB, DEDAB, and CHAPS.

In more detail, in order to increase fluorescence sensitivity in a sample in which protein his-mBFP including the affinity tag is contained at a low concentration, the detergent for dissociation of the above-mentioned quaternary structure was added to the reaction solution. As well known, since the quaternary structure of protein is maintained by noncovalent interactions (hydrogen, ion, hydrophobic force, and van der Waals force), in the case in which the detergent is added in a range in which a tertiary structure is not deformed, the quaternary structure may be dissociated into the monomers. Since structural quenching is small in NADPH bound to each of the dissociated monomers unlike the case in which NADPH bound in the quaternary structure, fluorescence may be increased. In the case in which 0.1% or less of SDS was added as the detergent in order to confirm the increase in the fluorescence, it could be confirmed that the fluorescence intensity is increased (2.5 to 3 times) as compared to a control group.

The present invention provides a assay method for a sample (specimen) using the detection method for NADP(H), or methods for detecting NADP(H) for measuring an activity of NADP(H) dependent enzyme.

In the present specification, the term "sample" may include cell extracts extracted from animal and plant intestines and tissues, water, soil, foods, supplies, wastes, or the like, but is not limited thereto.

In order to determine a content of NADPH in the biological sample, after crushing the sample, a supernatant containing NADPH was separated through the centrifugation and mBFP was added thereto, and then the content of NADPH was measured. As a result, in the case of $E.\ coli$, there reproducibly measured content of NADPH per 1 g of dried cell weight (gDCW) was 181.56 nM, and in the case of Yeast, the reproducibly measured content was 154.23 nM. Within 1 to 5 minutes after addition of protein, the content approached at the maximum value, and this value was confirmed as a significant value as compared to a literature value or a comparative experiment using other commercialized kits. Therefore, it could be confirmed that the measurement of NADPH in the biological sample according to the present invention may be used in all of the animal/plant sample, the environmental sample, and the like, as well as bacteria.

According to another exemplary embodiment of the present invention, there is provided a measuring method for an activity of NADP(H) dependent dehydrogenase or oxidoreductase using his-mBFP.

In more detail, after a substrate was added to the oxidoreductase having an NADP(H) dependent activity using his-mBFP to induce a reaction, an amount of the changed NADPH (NADP+ oxidized from NADPH, or reversely reduced NADPH) by the enzyme activity was measured, thereby measuring the enzyme activity (μmol/min/mg protein). Since this method uses a property that the substrate of oxidoreductase and NADPH are consumed at the same mole ratio, even in the case in which the substrate is not known, a specific activity may be measured from the amount of changed NADPH.

In the measuring method of the enzyme activity according to the present invention, NADPH in the reaction solution may be measured by adding his-mBFP within 1 minute, such that addition of an additional substrate is not required unlike the existing method of using fluorescent or luminescent substrate, and the method may be used under oxygen-free condition and at a low temperature, thereby making it possible to measure the enzyme activity with high reliability and sensitivity.

According to another exemplary embodiment of the present invention, there are provided a method of determining presence or absence of microbe and a method of indirectly quantifying the microbe using his-mBFP. In more detail, NADPH content in an environmental sample or food sample is measured using his-mBFP, such that the presence or absence of the microbe producing NADPH, and an amount of the microbe may be indirectly determined based on the measured content of NADPH per a specific microbe. The reason is that the reduced NADPH is produced only in the environment in which organisms exist or in vivo and even though the reduced NADPH exists in the sample, the reduced form disappears by the natural oxidation when organisms do not exist.

In the method of determining presence or absence of the microbe or indirectly quantifying the microbe according to the present invention, a culture time for forming a colony is not required, and there is no need for directly counting the number of microbes, such that pre-treatment may be rapidly performed and quantification may be easily performed. In this measuring method, the presence or absence of the microbe in the sample, which is an important indicator for determining a degree of environmental contamination, may be immediately confirmed, and a presence or absence of a latent contamination material may be confirmed by observing whether or not NADPH is increased after arbitrarily adding and culturing bacteria in the sample.

According to another exemplary embodiment of the present invention, there is provided a library screening method for selecting enzymes such as NADPH dependent dehydrogenase or oxidoreductase using his-mBFP.

In addition, the present invention provides a method of selecting NADPH dependent oxidoreductase inhibitor (anti-microbial agent) for dehydrogenase or oxidoreductase in the selected library.

In more detail, after total metagenome is extracted in an environmental sample and partially cut using Sau3A1, the library was prepared. The method is a method of culturing hosts having the prepared library, adding a specific substrate that is a target of activity screening and NADPH to induce a reaction, adding his-mBFP thereto, and then comparing the amount of changed NADPH, and through this method, a clone having related genetic resources may be screened from the library. In addition, after clones having dehydrogenase or oxidoreductase of the selected library were cultured and the substrate and NADPH were added thereto, reaction was induced in environment in which various chemical materials exist, and the amount of changed NADPH was determined using his-mBFP, thereby making it possible to select the activity inhibitor. As a relative value of the inhibitor drug, a half maximal inhibitory concentration ($IC_{50}$) value was calculated and used as an indicator.

According to another exemplary embodiment of the present invention, there is provided a method of stably storing his-mBFP for a long period of time.

Whether or not fluorescence activity is reduced by the method of storing purified his-mBFP aqueous solution was confirmed. As a result, when the solution was stored in a cold room at 4° C. for 2 months in a solution state without treatment of an additive for storage, fluorescence intensity was maintained at a level of 80% or more, and when mBFP solution to which glycerol having a final concentration of 50% was added was stored in a freezer at −80° C., the fluorescence intensity was maintained at a level of 90% or more. Since the mBFP according to the present invention does not require storage of a sensitive active site but requires only a protein structure capable of being bound to NADPH, unlike the enzyme having a catalytic function, the fluorescence may be maintained for a long period of time even in a condition in which the tertiary structure may be partially deformed. This advantage means that a kit may be easily stored and the kit may be sufficiently reused by only cold storage after opening.

The present invention provides a NADPH detection kit comprising metagenome-derived blue fluorescent protein, mBFP.

The kit according to the exemplary embodiment of the present invention may include a histidine tag (his-tag).

In addition, the kit according to the exemplary embodiment of the present invention may further include a detergent, a reducing agent, and a washing solution.

In addition, the kit may be used for recovering NADPH.

In the kit according to the exemplary embodiment of the present invention, NADPH may be recovered using affinity chromatography, but is not limited thereto.

In more detail, when a sample containing NADPH is loaded after mBFP or his-mBFP is fixed using a histidine binding carrier such as Ni-NTA, NADPH is bound to the carrier having the fixed protein according to binding force of NADPH. The resultant material is sufficiently washed with a general buffer, and then NADPH absorbed in a column is recovered using an elution buffer (20 mM Tris-HCl, 1-2 M NaCl, pH 7.5) containing a reducing agent (DTT or cysteine) for preventing oxidation of the reduced NADPH. In this case, salts (NaCl) added at a high concentration is used in order to dissociate NADPH from protein. In the case in which NADPH is extracted from biological sample by this method, there is no need for chemical synthesis of NADPH that is expensively sold, and NADPH of which biological stability is secured may be recovered from natural substances. Since the fixed protein-carrier may be reused dozens of times in a condition in which the protein is not deformed, a large amount of NADPH may be effectively recovered.

According to another exemplary embodiment of the present invention, there is provided a method of measuring a cell activity or dyeing tissue or organ using an amount of excellently expressed his-mBFP in vivo, binding force with NADPH, and fluorescence intensity increased after binding. More specifically, when a his-mBFP encoding gene is inserted into a specific vector and transformed into microbe, an animal cell, or a plant cell, fluorescence intensity dependent on the concentration of NADPH is exhibited, such that a concentration gradient of NADPH in the cell or a difference in activity may be confirmed as the fluorescence intensity. This process may be confirmed through an image by visualizing the transformed cell sample, tissue, or the like, using a fluorescence microscope or a confocal microscope. In the above-mentioned process, it may be confirmed that in the case of cancer cells, blue fluorescence is further increased as compared to normal cells, due to the increased NADPH in cancer cells relatively activated as compared to normal cells. See FIG. 14.

Advantageous Effects

In the detection method according to the present invention, unlike the existing quantitative measuring system, there is no need for addition of a substrate required for measurement or conversion of coenzymes, the method may be used at a low temperature at which activity of enzymes used in the existing measuring system is reduced, and fluorescent may be increased within a short time under an oxygen-free condition without consuming time for formation a fluorophore structure, such that the detection method may be widely used in various detection, quantifications, probes, diagnosis fields such as quantification of coenzyme in various ecological/environmental samples, measurement of the concentration of NADPH in vivo, measurement of movement and expressed amount of protein using them as the coenzyme, observation of interaction of protein by fusing a two hybrid system using the increased fluorescence during this process with a fluorescence resonance energy transfer (FRET) system, a kit for detecting physiological activity, and a biosensor, or the like.

In addition, the detection method according to the present invention may have economic advantages in that protein may be easily prepared with low cost on a large scale by using mBFP or his-mBFP having high expression ratio and solubility in *E. coli* as a NADPH fluorescence increasing reporter.

Further, in the detection method according to the present invention in which a basic problem of the widely used measuring system according to the related art using the enzyme activity is solved, when the detection method is used in various cell physiology, immunity, technology, and medicine, high efficiency and reliability may be implemented in a short time, such that the detection method may be widely utilized.

DESCRIPTION OF DRAWINGS

The above and other objects, features and advantages of the present invention will become apparent from the following description of preferred embodiments given in conjunction with the accompanying drawings, in which:

FIG. 1A shows a base sequence (SEQ ID NO: 2) of mBFP according to the present invention, and FIG. 1B shows an amino acid sequence thereof (SEQ ID NO: 1);

FIG. 2A shows a base sequence (SEQ ID NO: 4) of his-mBFP according to the present invention, and FIG. 2B shows an amino acid sequence thereof (SEQ ID NO: 3);

MODE FOR INVENTION

Hereinafter, the present invention will be described in more detail through specific Examples. However, the present invention is not limited to the following Examples, and it is obvious to those skilled in the art that various changes or modifications may be made within the idea and the scope of the present invention.

In this case, technical terms and scientific terms used in the present specification have the general meaning understood by those skilled in the art to which the present invention pertains unless otherwise defined. In addition, repetitive descriptions of the same technical configuration and action as those in the related art will be omitted.

Example 1

Preparation of his-mBFP Fused with his-Tag

In order to fuse an affinity tag for inducing over-expression of protein and efficient purification, an mBFP gene (SEQ ID NO: 2) was inserted in a pQE30 (Clonetech, USA, GenBank No. AF485783) vector mounted with his-tag, thereby preparing pQE30-mBFP.

mBFP included a Sph1 recognition site and was PCR-amplicated using a primer (5'-ATAGCATGCCAGAATCT-GAACG-3') (SEQ ID NO: 5) in which a start codon is removed and a primer (5'-ATAAAGCTTTCAAGCGGC-GAAGCCG-3') (SEQ ID NO: 6) having a BamHI recognition site. The amplified PCR fragment was cut by restriction enzymes Sph1 and BamHI and then inserted into pQE30 vector cut by the same enzyme to prepare pQE30-mBFP vector having his-mBFP gene (SEQ ID NO: 3) (See FIG. 4A).

In his-mBFP prepared by the process, unnecessary amino acid residue present in the vector may be included in his-tag and a protein encoding site. Since this structure may affect expression or functions of protein, recombinant protein in which six histidine residues are directly fused with the primer in front of the protein encoding site was prepared at the same time. To this end, a primer including an EcoR I recognition site and his-tag and a primer including only HindIII site were prepared, and PCR amplification was performed using pQE30-mBFP as a template.

Figure 3:
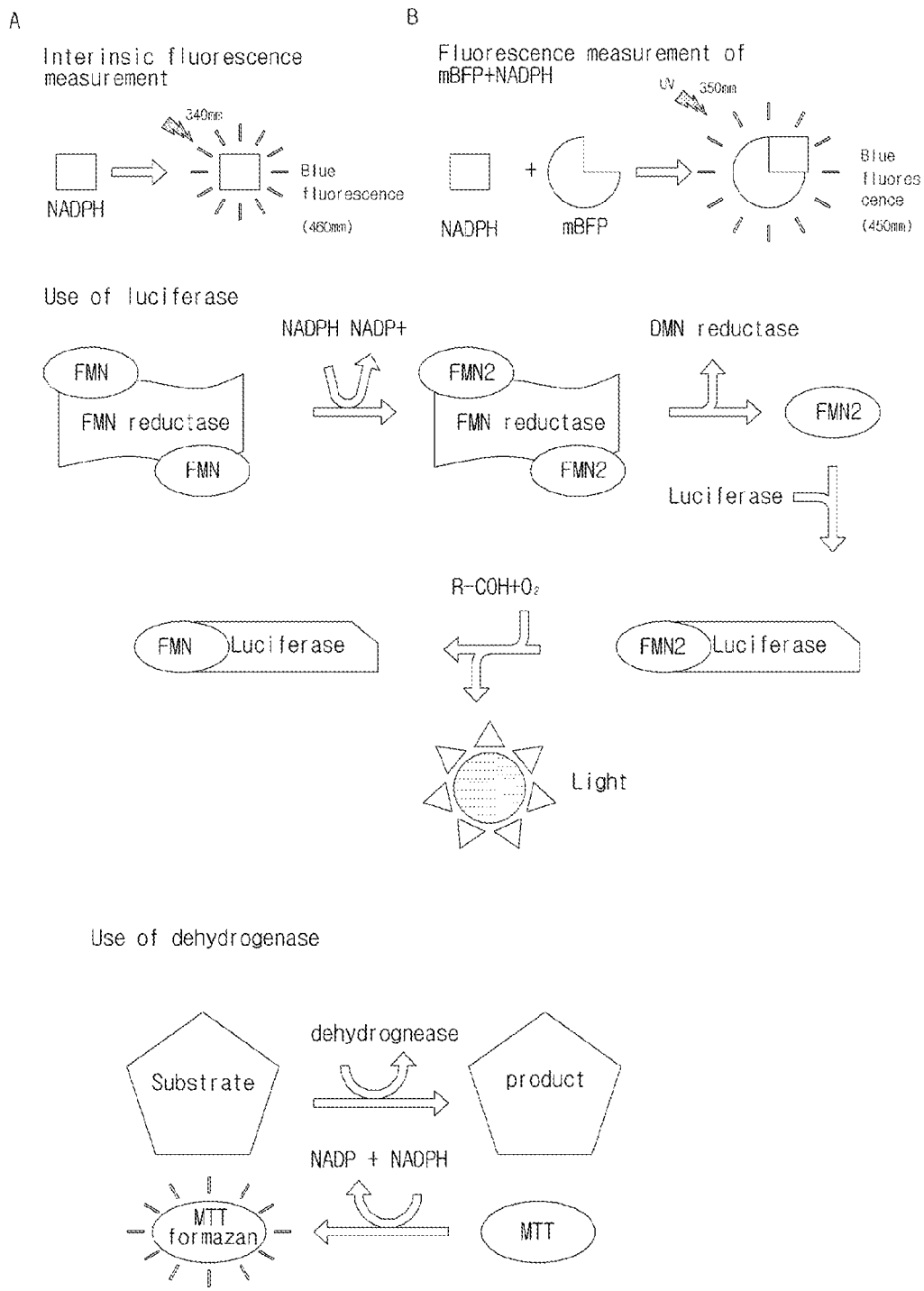
FIGS. 3A and 3B are diagrams for comparing an existing detection method for NADP(H) (See FIG. 3A) with methods for detecting NADP(H) according to the present invention (See FIG. 3B)
Figure 4:
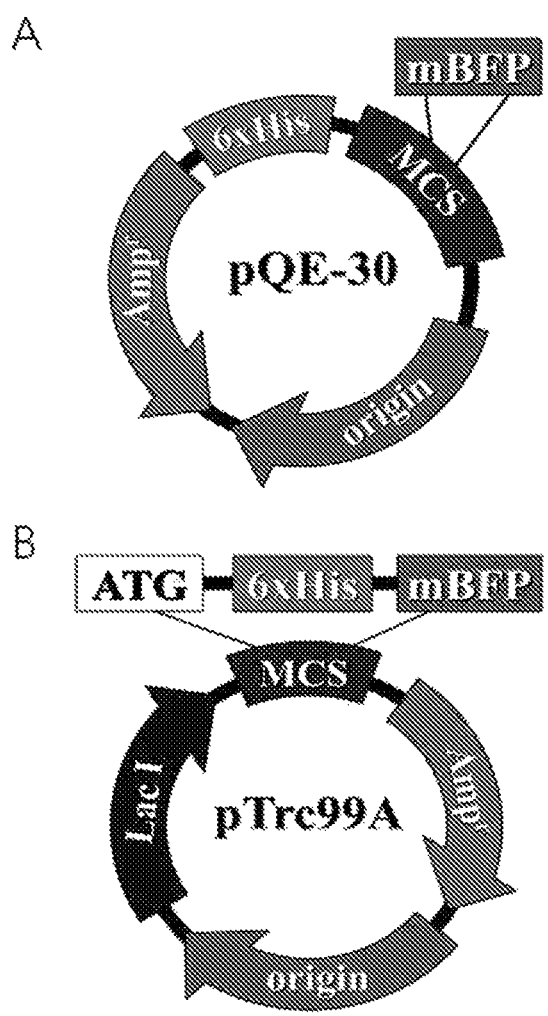
FIGS. 4A and 4B are schematic diagrams of vector for expressing his-mBFP according to the present invention;
(A: pQE30-mBFP, B: pTrc99A-his-mBFP)

The amplified fragments were cut by the restriction enzymes EcoRI and HindIII, and then inserted into pTrc99A vector (Pharmacia) cut by the same enzyme to prepare pTrc99A-his-mBFP (See FIG. 4B). The two kinds of prepared vectors having his-mBFP (pQE30-mBFP and pTrc99A-his-mBFP) were transformed into E. coli XL1-blue and BL21 as host.

As the host cell, any host cell known in the art may be used as long as the host cell may stably and continuously express the two kinds of vectors having his-mBFP. For example, E. coli JM109, RR1, LE392, W3110, or the like, may be used as the host. Since his-mBFP gene may be stably over-expressed in yeast Saccharomyces or Phichia, which are eukaryotic cells, these cells may be used as the host.

As a method of delivering the two kinds of vectors having his-mBFP in the host cell, in the case in which the host cell is a prokaryotic cell, a $CaCl_2$ method, a FSB solution treatment method, or an electric shock method may be used.

Further, in the case in which the host cell is the eukaryotic cell, the two kinds of vector having his-mBFP gene may be delivered into the host cell by the electric shock method, a liposome-mediated transformation method, or the like.

Example 2

Purification of his-mBFP (1) Strain Culture

A single colony transformed with pQE30-mBFP in Example 1 was inoculated into a liquid culture medium (LB+ 50 mg/ml of ampicillin) and pre-cultured for 12 hours under the condition of 37° C. and 200 rpm. When an absorbance value ($OD_{600}$) of the culture solution approach 2.0, the culture solution was inoculated into 1 L of the liquid culture medium (LB+50 mg/ml of ampicillin) and cultured for 8 hours, and then cell was recovered using a high-speed centrifuge. Here, in the case of mBFP having the his-tag, since it may be over-expressed without addition of a specific inducer, the mBFP having the his-tag has an advantage in that a chemical additive for inducing expression is not required.

(2) Separation of Protein Using Binding Capacity of his-mBFP to NADPH mBFP was purified and separated using cibacron blue used in affinity chromatography of protein bound to NADPH.

The cibacron blue, which is a kind of chlorotriazine pigments, has a capacity of specifically binding to enzymes using NAD(H), NADP(H), or the like, to be mainly used to purify protein. After the cells recovered as described above were suspended in 50 ml of binding buffer (20 mM Tris-HCl, pH 7.5), the cells were disrupted by repeating a process of applying an ultrasonic wave for 10 seconds and then being released for 30 seconds 10 times using an ultrasonicator.

Insoluble precipitation materials were removed from the disrupted cells using a high speed centrifuge (15,000 rpm, 15 min), and then a supernatant including soluble protein was recovered. In order to remove macromolecules such as chromosomes, polysaccharides, and the like, remaining in the recovered supernatant, 1 g of cell debris remover (CDR) was added per 20 ml of supernatant and mixed at a low temperature for 10 minutes, followed by centrifugation (15,000 rpm, 30 min), and then remaining impurities were removed using a syringe filter (0.45 μm). The binding buffer having a volume 10 times larger than that of the cell disrupted solution pre-treated as described above was added thereto and diluted.

A process of purifying his-mBFP from the diluted solution was as follows.

First, an affinity carrier was sufficiently washed with 50 ml of binding buffer so as to reach equilibrium. After cell disrupted solution was flowed at a flow rate of 2 ml/min thereto to induce attachment of protein, 100 ml of washing buffer (20 mM Tris-HCl, pH 7.5) was flowed at a flow rate of 4 ml/min, such that protein not bound to the column and impurities nonspecifically and weakly bound to the column were removed. An elution buffer (20 mM Tris-HCl, 2M NaCl, pH 7.5) was flowed at the same flow rate to the prepared sample, such that proteins absorbed in the affinity resin were recovered.

After a fraction in which his-mBFP was recovered was confirmed by fluorometer analysis, in order to remove highly concentrated NaCl contained in the elution solution, buffer was exchanged using a centri-prep (cut-off size 10 kDa).

Figure 5:
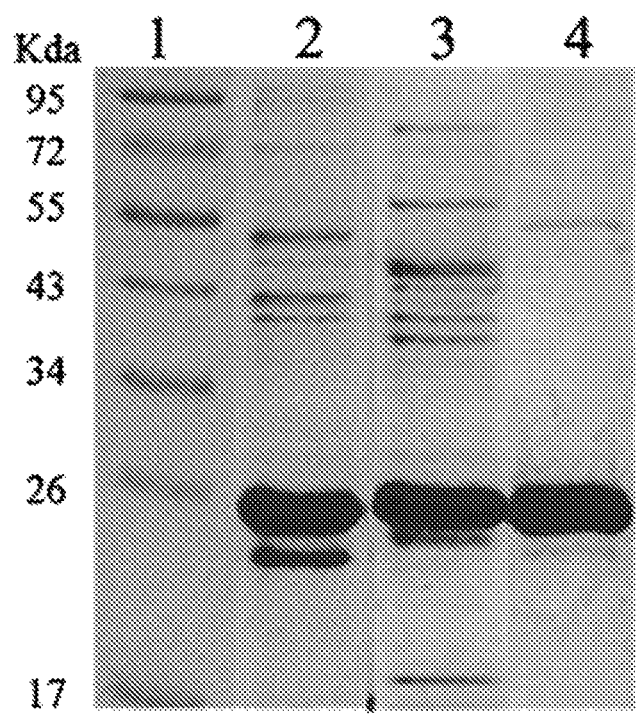
FIG. 5 is a diagram for analyzing purity of his-mBFP according to the present invention that is separated by an affinity chromatography using sodium dodecyl sulfate polyacrylamide gel electrophoresis (SDS-PAGE);
(Lane 1, size marker; lane 2, his-mBFP separated using a cibacron blue resin; lane 3, his-mBFP separated using Ni-NTA; lane 4, his-mBFP continuously separated using cibacron Blue resin and Ni-NTA resin)

The recovered solution was confirmed using SDS-PAGE, and as a result, his-mBFP having a purity of 80% or more may be separated as shown in lane 2 of FIG. 5.

(3) Purification of his-mBFP Using Metal Affinity Chromatography

As described above, protein may be purified by a method of using properties such as binding force between the tertiary structure and a specific substrate, surface charges, hydrophobicity, or the like, or fusing an affinity tag.

Among them, since his-tag has a metal affinity, his-tag is known as a representative tag capable of being fused various proteins and using affinity chromatography (Ni-NTA). After his-tag is fused with mBFP so as to complement the purification method of using the NADPH binding force or separate mBFP protein through an independent process, purification was performed by the following methods.

After the cells recovered according to the above-mentioned process were suspended in 50 ml of binding buffer (20 mM Tris-HCl, 500 mM NaCl, pH 7.5), the cells were disrupted by repeating a process of apply an ultrasonic wave for 10 seconds and then being released for 30 seconds 10 times using an ultrasonicator. Insoluble precipitation materials were removed from the disrupted cells by high speed centrifugation (15,000 rpm, 10 min), and then a supernatant including soluble protein was recovered. Macromolecules such as chromosomes, polysaccharides, and the like, remaining in the recovered supernatant was removed by adding 1 g of cell debris remover (CDR) per 20 ml of supernatant to induce a reaction and then performing centrifugation as described above or using a syringe filter (0.45 μm) to remove impurities.

The binding buffer having a volume 10 times larger than that of the supernatant in which the impurities were removed was added thereto and diluted. The Ni-NTA resin to be used as the affinity chromatography was sufficiently washed with 50 ml of the binding buffer so as to reach equilibrium. After the protein solution was flowed at a flow rate of 2 ml/min therein to induce attachment, 100 ml of washing buffer (20 mM Tris-HCl, 500 mM NaCl, 10 mM imidazole, pH 7.5) was flowed at a flow rate of 4 ml/min, such that protein not bound to the column and impurities nonspecifically and weakly bound to the column were removed. Elution of protein was performed by flowing an elution buffer (20 mM Tris-HCl, 500 mM NaCl, 250 mM Imidazole, pH 7.5) at a flow rate of 2 ml/min.

After a fraction in which the fluorescent protein was recovered was confirmed by fluorometer assay, in order to remove the added NaCl for reducing interaction between imidazole added to the elution buffer and nonspecific protein, a filter (cut-off size 10 kDa) was used. The separated solution was confirmed using SDS-PAGE, and as a result, protein having a purity of 85% or more may be confirmed as shown in lane 3 of FIG. 5.

(4) Purification of his-mBFP Continuously Using Affinity Chromatography

Each of the above-mentioned affinity chromatography has sufficient separation capacity, but absolute purification capable of obtaining a purity of about 100% may be required in some cases. This purity may not be obtained by each of the above-mentioned processes in which biological interference materials are present, but in the case in which the above-mentioned processes are continuously performed, this purity may be obtained.

Therefore, the two affinity chromatography, that is, cibacron blue and Ni-NTA resin were continuously performed, thereby purifying his-mBFP.

After the supernatant sample in which soluble protein was prepared similarly to the above-mentioned processes, the sample was flowed into cibacron blue reached the equilibrium by binding buffer (20 mM Tris-HCl, pH 7.5) at a flow rate of 2 ml/min to induce attachment of protein, and 100 ml of washing buffer (20 mM Tris-HCl, pH 7.5) was flowed at a flow rate of 4 ml/min, such that protein not bound to the column and impurities nonspecifically and weakly bound to the column were removed. The attached protein was recovered using a buffer (20 mM Tris-HCl, 2 M NaCl, pH 7.5) containing highly concentrated salts.

After a fraction in which mBFP was recovered and a purity were confirmed by SDS-PAGE assay, a metal affinity resin column for removing contaminated protein that was simultaneously eluted was performed. To this end, the recovered protein solution was diluted 4 times and flowed to the Ni-NTA resin reached equilibrium by 50 ml of binding buffer at a flow rate of 2 ml/min, thereby inducing attachment of protein. Protein not bound to the column and impurities nonspecifically and weakly bound to the column were removed by flowing 100 ml of washing buffer (20 mM Tris-HCl, 500 mM NaCl, 10 mM Imidazole, pH 7.5) at a flow rate of 4 ml/min. The proteins absorbed in the Ni-NTA resin were recovered using the buffer (20 mM Tris-HCl, 500 mM NaCl, 250 mM Imidazole, pH 7.5).

After a fraction was confirmed using a fluorometer, a desalting column was used to remove imidazole and NaCl that remain in the elution solution. The recovered solution was confirmed using SDS-PAGE, and as a result, protein having a high purity of 95% or more may be confirmed as shown in lane 4 of FIG. 5.

Figure 6:
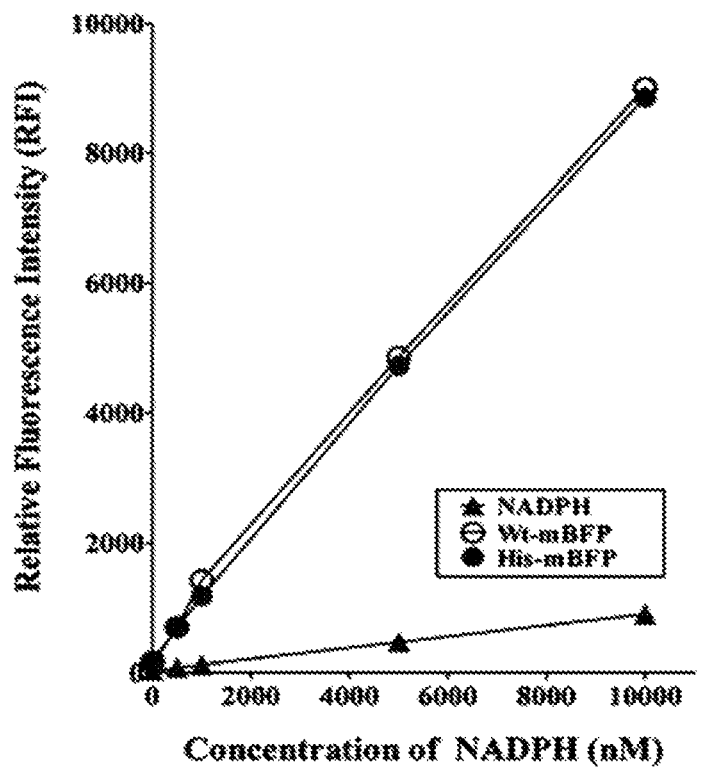
FIG. 6 is a graph comparing changes in fluorescence intensity between wild-type mBFP and his-mBFP according to the present invention.

In addition, as shown in FIG. 6, it could be confirmed that since there was no difference between fluorescence of his-mBFP having a purity of 95% or more and fluorescence of wild-type protein to which the affinity tag is not attached, there is no problem in a process of measuring activities of NADP(H) or HADP(H) dependent enzymes.

Example 3

Establishment of Optimum Reaction Conditions for Quantifying NADPH Using his-mBFP (1) Measurement of Fluorescence of his-mBFP According to Temperature Change In order to confirm dependency of fluorescence of his-mBFP on a temperature by binding with NADPH, 0.9 ml of mBFP solution separated in Example 2 was released in water baths adjusted at temperatures of 4, 10, 20, 30, 37, 45, and 55° C., respectively, for 1 hour, and then 0.1 ml of NADPH was mixed at each of the concentrations to perform reaction.

The measurement of fluorescence was determined as fluorescence intensity emitted at 450 nm after excitation at 350 nm using a fluorometer.

Figure 7:
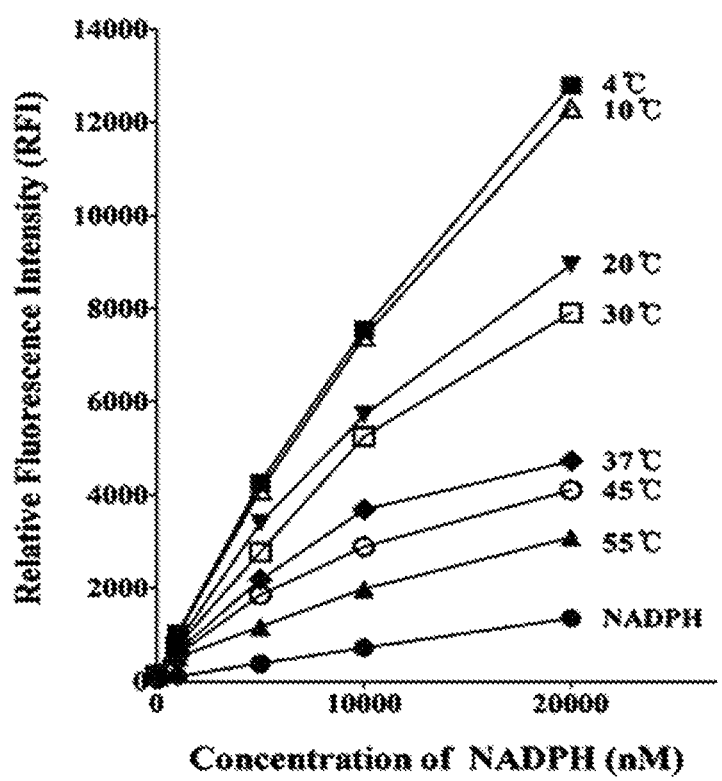
FIG. 7 is a graph showing results obtained by measuring changes in fluorescence intensity of his-mBFP of the present invention according to temperature changes.

As a result, it could be appreciated that the fluorescence intensity according to each of the temperature decreases as the temperature increases as shown in FIG. 7.

More specifically, linear reaction characteristics according to the concentration of NADPH may be confirmed at 4 to 10° C. and a NADPH concentration of 10 nM to 10 μM, at 20° C. and 37° C. and at a NADPH concentration of 10 nm to 5 μM, and at 45° C. and 55° C. and a NADPH concentration of 100 nM to 1 μM.

(2) Measurement of Fluorescence of his-mBFP According to pH of Buffer

In order to confirm fluorescence variations and intensity by the buffer in a process of measuring NADPH using his-mBFP, 0.5 ml of purified his-mBFP solution (5 μM, 20 mM Tris-HCl buffer, pH 7.5) was mixed with 0.4 ml of each buffer (100 mM) and 0.1 ml of NADPH at each concentrations to perform reaction. In this case, final concentrations of the used buffers were as follows.

Figure 8:
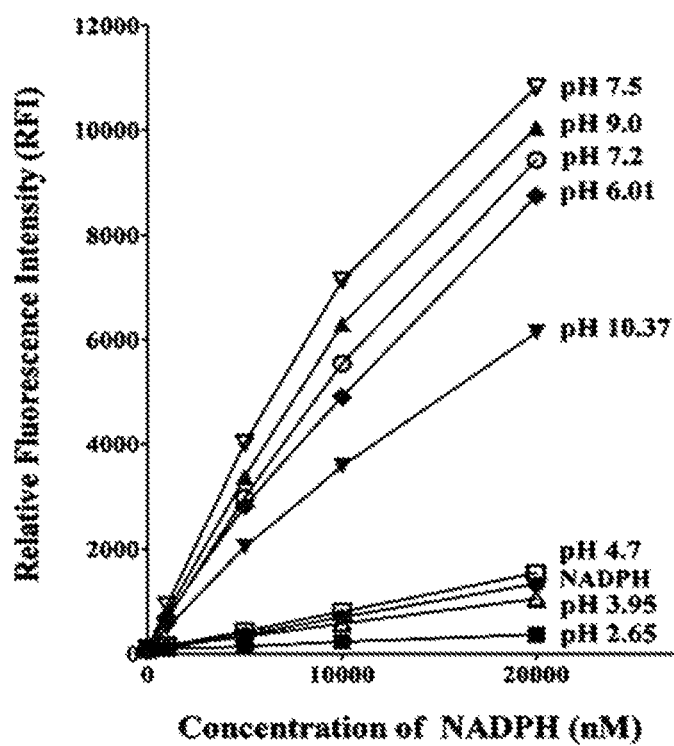
FIG. 8 is a graph showing results obtained by measuring changes in fluorescence intensity of his-mBFP of the present invention according to pH changes of a buffer.

Optimum Concentration and pH of Buffer 40 mM Tris-HCl (pH 7.5), 40 mM sodium-phosphate (pH 6.01), 40 mM carbonate-bicarbonate (pH 10.37), 40 mM PBS (pH 7.2), 40 mM glycine-NaOH (pH 9.0), 40 mM citric acid-sodium citrate (pH 4.71), 40 mM acetic acid-sodium acetate (pH 3.95), 40 mM citric acid-phosphate buffer (pH 2.65) As a result, in the fluorescence intensity of mBFP according to each of the buffer, distinct linear sections appeared according to the concentration of NADPH in a wide range from weak acid buffer to base buffer as shown in FIG. 8. In addition, although not significant, it could be observed that the fluorescence is reduced in the acid buffer, such that a gradient of the linear section is reduced.

The fluorescent intensity was highest in 40 mM Tris-HCl (pH 7.5). The significant linear reaction characteristics were confirmed at a NADPH concentration of 10 nM to 10 μM in 40 mM Tris-HCl (pH 7.5), 40 mM glycine-NaOH (pH 9.0), and 40 mM PBS (pH 7.2), and NADPH may be reproducibly measured in a concentration range of 10 nM to 1 μM in 40 mM sodium-phosphate (pH 6.01) and 40 mM carbonate-bicarbonate (pH 10.37) buffer. In experiments in which the concentration of each of the buffer is corrected to a final concentration of 20 mM, the same result was obtained. Therefore, it was confirmed that the salt concentration determining pH at which the reaction was stably performed is 20 to 40 mM.

(3) Measurement of Fluorescence of his-mBFP According to Reaction Time

In order to measure a time at which his-mBFP exhibits maximum fluorescence after binding to NADPH, 0.9 ml of purified his-mBFP solution (5 μM, 20 mM Tris-HCl buffer, pH 7.5) was released in a water bath at 30° C. to reach equilibrium, 0.1 ml of NADPH was added thereto at each of the concentration and then, fluorescence intensity according to the reaction time was measured.

Figure 9:
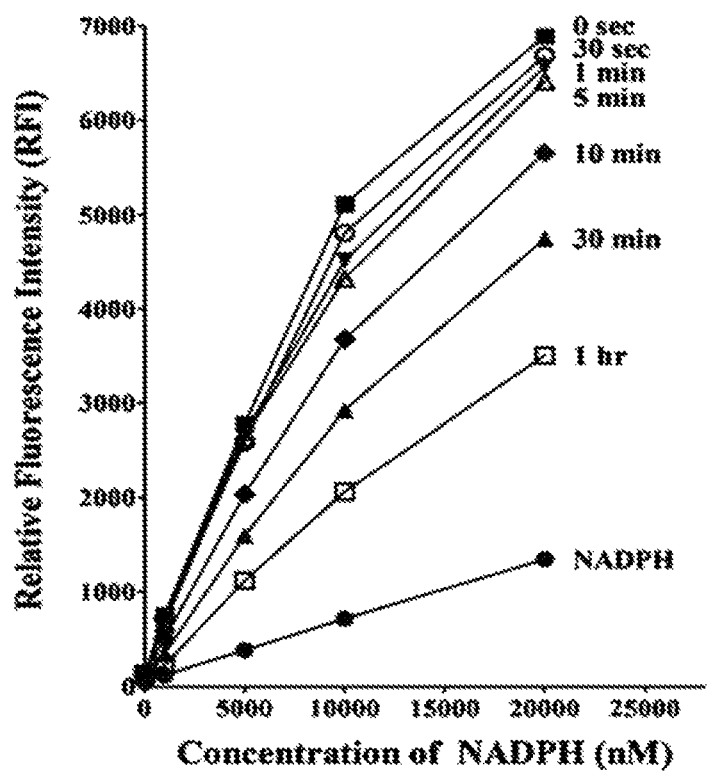
FIG. 9 is a graph showing results obtained by measuring changes in fluorescence intensity of his-mBFP of the present invention according to reaction time.

As a result, it was confirmed that the maximum fluorescence is sufficiently induced within 30 seconds to 5 minutes and fluorescence may be stably and reproducibly measured within about 1 minute as shown in FIG. 9.

Unlike other methods known in the art in which enzymes inducing color reaction or having activity are coupled, it was shown that the absolute value tends to be reduced as time goes on. This property, which is a phenomenon associated with the natural oxidation of NADPH of which chemical stability may be rather reduced as time goes on, is a result showing the advantage of rapid measuring method according to the present invention.

Reduction of fluorescent with the passage of time has an effect of reducing sensitivity, but linear values were significantly confirmed within a predetermined time. Therefore, it could be confirmed that the method according to the present invention has the maximum sensitivity within 1 minute but may be significantly used in other time ranges. This means that in the case in which a suitable standard curve is obtained and used in an experiment after a reaction time is determined according to an amount of sample, there is no difference in quantified values by time.

(4) Measurement of Blue Fluorescence According to Protein Concentration

In order to measure fluorescence intensity according to the protein concentration of his-mBFP and measuring sensitivity of NADPH, 0.9 ml of his-mBFP solutions (20 mM Tris-HCl buffer, pH 7.5) having each of the concentrations of 0.1 μM, 0.5 μM, 1 μM, 5 μM, 7 μM, and 10 μM and 0.1 ml of NADPH having each of concentrations were mixed to perform the reaction.

Figure 10:
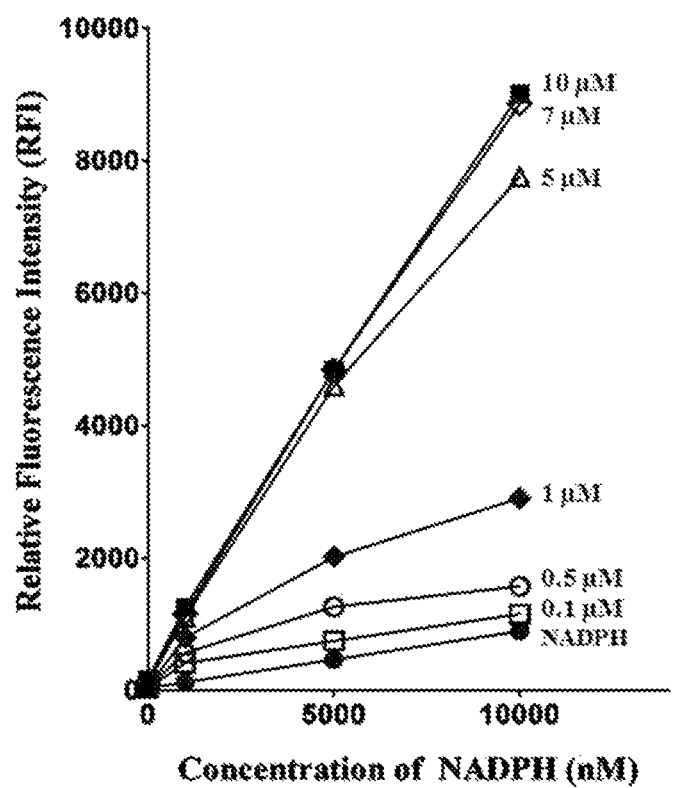
FIG. 10 is a graph showing results obtained by measuring changes in fluorescence intensity according to concentrations of his-mBFP of the present invention.

As a result, it could be appreciated that the fluorescence intensity according to each of the concentration of mBFP is reduced as the concentration reduced as shown in FIG. 10.

More specifically, the fluorescence intensity was significantly measured at a protein concentrations of 7 μM and 10 μM, and the fluorescence intensity was significantly reduced at a protein concentration of 1 μM or less.

The linear reaction characteristics according to NADPH concentration were shown at a protein concentration of his-mBFP of 7 to 10 μM and a NADPH concentration of 10 nM to 10 μM, a protein concentration of his-mBFP of 5 μM and a NADPH concentration of 10 nM to 5 μM, a protein concentration of his-mBFP of 1 μM and a NADPH concentration of 10 nM to 1 μM, and a protein concentrations of his-mBFP of 0.1 and 0.5 μM and a NADPH concentration of 10 nM to 0.5 μM.

As the results, it may be confirmed that the present invention has an advantage in that NADPH may be reproducibly measured using protein maximally diluted 100 times according to the NADPH concentration to be estimated in a sample to be measured, or the sample may be diluted to be used after a concentration of his-mBFP protein is minimized.

Example 4

Method of Increasing Measuring Sensitivity of his-mBFP in Sample Having Low NADPH Concentration As shown in the Examples, it was confirmed that in the case of his-mBFP, NADPH may be accurately measured at various concentrations of 10 nM or more.

However, in the case in which an amount of sample is limited or activity of NADPH-dependent enzyme having low activity is measured, a method capable of sensitively measuring a trace amount of NADPH may be required.

The present inventors tried to search the method and designed a method of increasing the sensitivity based on the fact that his-mBFP has a tetramer structure having four subunits. That is, the present inventor assumed that in the case in which the four subunits are dissociated by a method in which deformation of binding site with NADPH is not induced, the four molecular constructs having NADPH bound to each of the four molecular constructs may be formed, which may reduce fluorescence interference or quenching as compared to circular portion in which 4 subunits are bound, thereby increasing fluorescence. In order to confirm the assumption, a small amount of SDS (0.01%) capable of separating the protein tetramer was added to purified mBFP solution (5 μM, 20 mM Tris-HCl buffer, pH 7.5) and mixed with 0.1 ml of NADPH 1 μM to perform the reaction.

Figure 11:
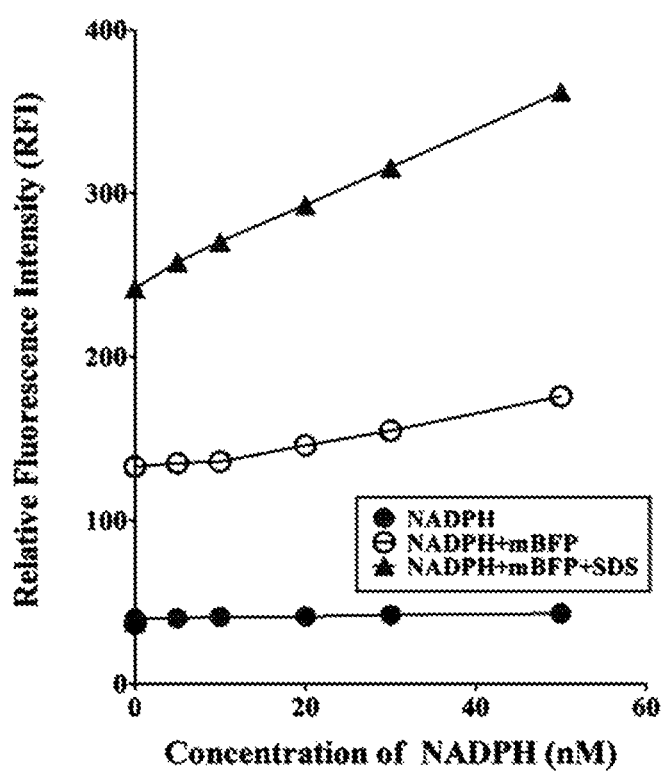
FIG. 11 is a graph showing results obtained by measuring changes in fluorescence intensity of his-mBFP of the present invention according to addition of detergent (SDS)

As a result, it was confirmed that in the case in which SDS is added, the fluorescence value is increased 2.4 to 3.1 times as compared to a control group having the same amounts of his-mBFP and NADPH as shown in FIG. 11. More specifically, it was observed that the fluorescence intensity is increases 3.1 times at a NADPH concentration of 50 nM and 2.4 times at a NADPH concentration of 10 nM as compared to that of the control group in which SDS is not included.

Through the results, it could be confirmed that in the case of performing treatment using a detergent containing SDS in order to enlarge a measuring range, the fluorescence of NADPH having a concentration of 100 pM or more may be measured at the same protein concentration. As the detergent that may be used in this process, it was confirmed that all of an ionic detergent represented by SDS and a non-ionic detergent represented by Triton X-100 or Tween 20 have similar effect in a suitable concentration range (0.01 to 1%).

Example 5

Retention of Fluorescence of his-mBFP According to Storage Method

In order to search a long-term storage method for his-mBFP requiring retention of the structure that is an important factor in fluorescence activity, suitable protein storage methods were observed. As storage conditions, degrees of reduction of fluorescence according to time were confirmed at different temperatures (4° C., −20° C., −80° C.) and different concentrations of additives for storage (5% trehalose, 25% glycerol, 50% glycerol, based on final concentration).

Among his-mBFP samples stored under each of the conditions, in the case of frozen samples, the sample was sufficiently hydrated in a cool buffer for 5 to 45 minutes in consideration of reconstruction of the structure, time required for restoration, or the like, and then was used in the experiment.

Figure 12:
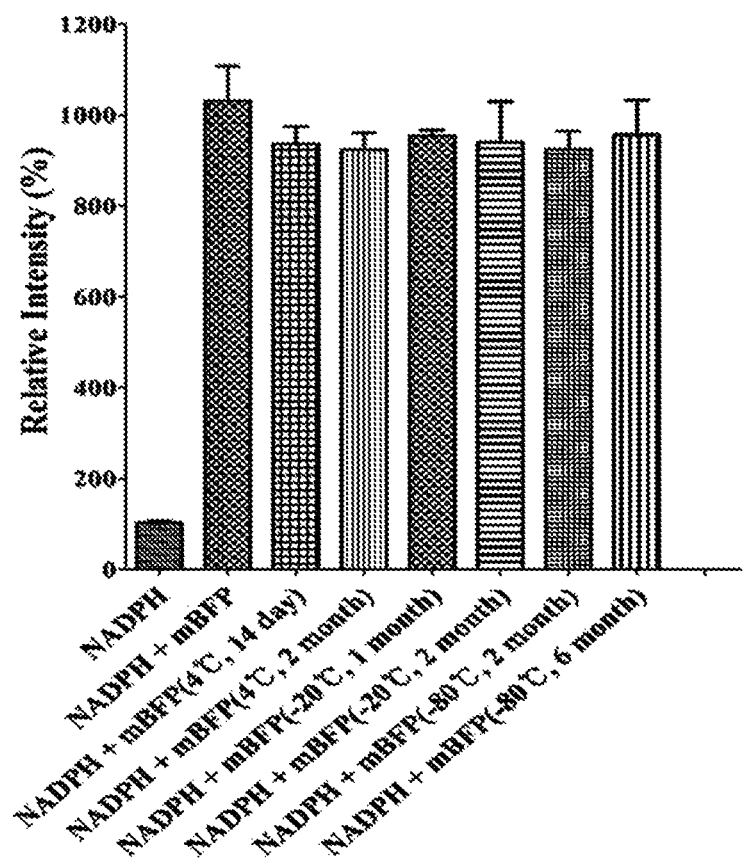
FIG. 12 is a graph showing results obtained by measuring a retention degree of fluorescence activity of his-mBFP of the present invention according to a storage method.
Figure 13:
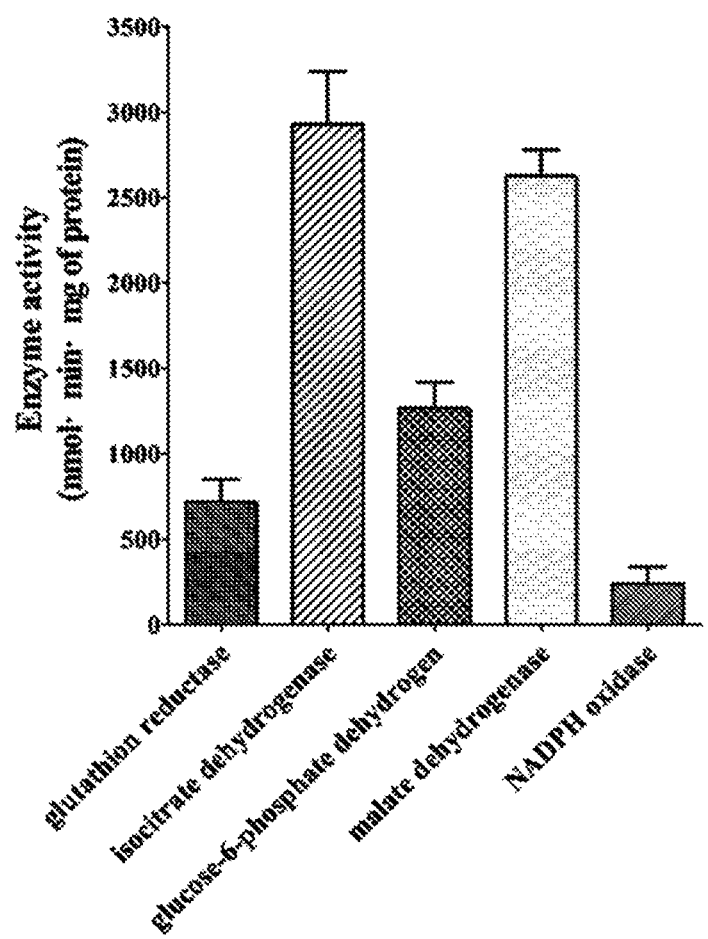
FIG. 13 is a graph showing results obtained by measuring activities of NADP(H) dependent enzyme using his-mBFP of the present invention.

As a result, the fluorescence of the stored protein was maintained at a level of about 80% or more in both cool and frozen conditions after 6 months as shown in FIG. 12.

More particularly, it could be confirmed that in the case in which the sample is stored in a cold room at 4° C. for 2 months in a solution state without treatment of an additive for storage, the fluorescence of the protein is maintained at a level of 80% or more, and when the sample is stored in a freezer at −20 to −80° C. for 2 months with an additive for storage, the fluorescence of the protein is maintained at a level of 95% or more.

It was observed that in the case of the sample after 6 months, when the additive (25% to 50%) is added, the fluorescence is maintained at a level of 90% or more, but in the case of the cold sample, the fluorescence was reduced to a level of 65 to 70%.

Through the result, it could be confirmed that cold storage may be sufficient for short-term storage within 2 months and it may be advantageous to freezing the sample together with the additive for long-term storage. Therefore, it could be appreciated that the storage method may be different whether a NADPH assay kit is prepared in a liquid state or a freeze-dried state, and in the case of the freeze-dried sample, the sample may be stored for about 2 months after hydration and reused to measure NADPH.

It was confirmed that as the additive, EDTA, NaCl, KCl, cysteine, dithiothreitol (DTT), or the like, has a partial effect as well as the above-mentioned additive, and there is no large variation in storage containers or buffers.

Example 6

Certification Method of NADPH Concentration in Biological Sample (1) Detection Method for NADPH Concentration In Vivo Using his-mBFP In order to confirm whether a content of NADPH is accurately measured in the biological sample under the optimum reaction conditions, single cellular tissues such as Escherichia coli (E. coli) XLI-blue and Candida albicans NUM678 and multicellular tissue such as bean leaf and rabbit tissue were prepared as samples and disrupted, and then a supernatant containing NADPH was separated by centrifugation and added with his-mBFP, thereby certificating the amount of NADPH.

More specifically, in the case of Escherichia coli (E. coli) XLI-blue and Candida albicans NUM678, the microbes were cultured by the same method as that in Example 2, followed by repeating a process of rapidly freezing the culture sample using liquid nitrogen and thawing the frozen sample in ice 3 times. Next, the cell was disrupted using a sonicator, and then the supernatant was separated using a centrifuge (15,000 rpm, 30 min).

20 mM Tris-HCl (pH 7.5) having a volume 3 times larger than that of the supernatant was added to the separated supernatant and diluted, and the resultant was used as a certification sample.

In the case of other biological samples (tissues of animal or plant), after the tissue was sliced and rapidly frozen in liquid nitrogen, 1 ml of homogenizing buffer (10 mM phosphate buffer, pH 7.4) was added per 30 mg of each tissue, and then disruption was induced by grinding for 1 to 5 minutes using a homogenizer. The high-speed centrifugation (15,000 rpm, 30 min) was performed on the prepared sample, and a supernatant was recovered and used as the sample.

In the case of all of the samples, the sample was diluted or concentrated based on an estimate value of NADPH known in the literature to be used in measurement, and the measured value was calculated by moles per dry weight (nmol/gDCW).

As a result, the amount of NADPH per dry weight was similar to or higher than the known estimate value as shown in the following Table 1. These results show that the method according to the present invention may have reliability and a difference in rapid measurement (measurement within a short time in which the natural oxidation is not generated) from the existing method.

TABLE 1

| Sample | NADPH (nmol/gDCW) |
| --- | --- |
| E. coli | 181.56 ± 25 |
| Yeast | 133.02 ± 15 |
| Bean leaf tissue | 232.56 ± 45 |
| Rabbit tissue | 176.12 ± 30 |

(2) Reliability and Reaction Time Comparison with NADPH Assay Kit Commercialized and Sold in the Market In order to compare the detection method for NADPH using his-mBFP according to the present invention and the commercialized NADPH assay kit with each other, a supernatant containing NADPH was extracted using E. coli and yeast as samples, and measuring capability was compared.

As comparison targets, two kinds of commercialized NADPH assay kits (BioVision Co. Catalog K347-100 and Enzychrom Co. Catalog ECNP-100) were used.

Describing each of the kits in more detail, after the microbe was cultured by the same method as that in Example 2, samples of E. coli and Yeast were put into PBS solution according to a description provided from BioVision Co., followed by centrifugation and washing. Next, NADPH extracted buffer was added, cells were disrupted, and then supernatants were recovered.

The sample was released in water bath (60° C.) for 30 minutes, the pre-treated supernatant and NADP Cycling Mix in which 98 μl of NADP cycling buffer and 2 μl of NADP Cycling Enzyme Mix were mixed were put into a 96 well plate to perform reaction for 5 minutes, and then 10 μl of NADPH developer was added thereto to induce reaction for 4 hours. Finally, absorbance was measured using light having a specific wavelength (OD 450 nm) and a spectrophotometer.

In the case of the kit provided from EnzyChrom Co., samples containing NADPH were extracted from the E. coli and Yeast by the method as described above, the extracted samples and prepared enzyme reaction buffer (60 μl assay buffer, 1 μl enzyme mix, 10 μl glucose, and 14 μl MTT) were put into the 96 well plate and mixed to perform reaction for 30 minutes, and then absorbance was measured at OD 565 nm.

In the detection method according to the present invention, after only his-mBFP was added according the above-mentioned optimum condition (addition of only 1 to 5 μM protein), a fluorescence value was immediately measured without additional reaction time (<1 min).

As a result, it could be confirmed that in the case of using the detection method according to the present invention, the fluorescence value was repeatedly exhibited to be about 129 to 132% higher than the value averagely measured in the existing kit as shown in the following Table 2.

This result was obtained by the following reasons. In the detection method using his-mBFP according to the present invention, measurement may be rapidly performed, complicated pre/post treatment was not required, and a time required to induce the reaction was not required since a catalytic enzyme was not added, such that reduction of NADPH by natural oxidation or reaction with other inference enzymes was not generated.

Therefore, this result shows that the disadvantage of the existing commercialized kits that it was impossible to directly quantify NADPH in initial samples may be solved by the detection method according to the present invention and a value that is closer to an actual value may be implemented.

In addition, a degree at which the measured value may implement the actual value was reconfirmed by a spiking assay (NADPH having a known concentration was added to a predetermined amount of a sample and re-measured according to a kit, such that capacity of accurately measuring an amount of the added NADPH was compared).

TABLE 2

| Sample | mBFP NADPH Kit (nmol/gDCW) | [a]Existing NADPH Kit (nmol/gDCW) |
| --- | --- | --- |
| E. coli | 180.55 ± 25 | 137.78 ± 20 |
| Yeast | 132.98 ± 15 | 102.52 ± 10 |

[a]An average value of measured values in two kinds of kits and a standard deviation was shown. Each of the commercialized kits had similar measured level at a level of about 10%.

Example 7

Method of Measuring Activity of Specific Enzyme Having NADPH Dependent Activity A method of measuring the activity capable of measuring physiologic activities of useful enzymes or biological enzymes using NADPH as a co-activator (in the case in which NADPH is used as an electron donor, the decreased fluorescence was measured, and in the case in which NADP+ is used as an electric acceptor, the increased fluorescence was measured) using an increase in NADPH dependent fluorescence intensity by his-mBFP was constructed.

To this end, after a substrate was added to the oxidoreductase having NADP(H) dependent activity to induce a reaction, an amount of changed NADPH (NADP+ oxidized from NADPH, or reversely reduced NADPH) by the enzyme activity was measured, thereby measuring the enzyme activity (μmol/min/mg protein). At the same time, as a method of determining presence or absence of a specific substrate and quantifying the substrate, a method of adding his-mBFP and a suitable amount of NADPH to a sample, inducing a reaction of oxidoreductase, and calculating an amount of changed NADPH to quantify the existing substrate was constructed. This method is based on the fact that a kinetic property of all of the NDAPH dependent oxidoreductases is that a mole ratio of consumed substrate is the same as that of NADPH. Construction and reliability evaluation of the method of measuring the activity was certified using the following commercialized enzymes. A reaction rate was calculated using a gradient at a time point at which a decrease of fluorescence is constant for a predetermined time (5 to 20 minutes).

As an example of typical reactions, first, 0.02 units of glutathione reductase was reacted with 50 mM potassium phosphate buffer (pH 7.5) containing 5 mM of oxidized glutathione (GSSG) and 2 mM NADPH at room temperature, and then fluorescence was measured. In addition, 0.03 units of isocitrate dehydrogenase was reacted with 50 mM phosphate buffer (pH 7.2) containing 5 mM isocitrate, 2 mM $MgCl_2$, and 2 mM NADP+ at room temperature, and then fluorescence was measured. In addition, 0.02 units of glucose-6-phosphate dehydrogenase was reacted with 50 mM Tris-HCL buffer (pH 7.5) containing 5 mM glucose-6-phosphate, 50 mM $MgCl_2$, and 2 mM NADP+ at room temperature, and then fluorescence was measured. Further, 0.04 units of malate dehydrogenase was reacted with 50 mM Tris-HCL buffer (pH 7.5) containing 5 mM L-malate, 50 mM $MgCl_2$, and 2 mM NADP+ at room temperature, and then fluorescence was measured. In addition, 0.02 units of NADPH oxidase was reacted with 50 mM phosphate buffered saline (PBS) containing 50 mM $MgCl_2$ and 2 mM NADP+ at room temperature, and then fluorescence was measured. At the time of measuring the fluorescence, the reaction solution was diluted in consideration of mole ratio with his-mBFP.

1 unit of the enzymes means an amount of the enzyme capable of oxidizing 1 μmole NADPH to NADP+ or reducing NADP+ on the contrary at 25° C.

As a result, increases or decreases in fluorescence corresponding to activities of all of the enzymes added early during all of the experimental process were accurately measured. Finally, in the case of an enzyme of which activity is not known, after a change in fluorescence value was measured by the same process and converted into an oxidation rate of a substrate to determine the activity, when the determined activity and a result obtained by analyzing the reduced substrate using HPLC and MS were compared with each other, it was confirmed that the activity calculated from the change in fluorescence value and the activity measured from the change in the substrate are the same.

The above-mentioned result certifies that at the time of measuring an activity of any enzyme using NADPH or NADP+, when only 1 to 5 μM his-mBFP is add, and then a change in fluorescence value is measured, a specific activity of the enzyme may be accurately and rapidly measured. Examples of an important enzyme that may be measured by the above-mentioned process include nitric oxide synthase, thioredoxin reductase, glutathione dependent oxidoreductase, NADPH dehydrogenase, succinate:ubiquinone oxidoreductase, plasma membrane oxidoreductase, cytochrome c oxidoreductase, oxoglutarate oxidoreductase, ferredoxin-NADP+ reductase, D-xylulose reductase, aldose reductase, alcohol dehydrogenase, glucose-fructose oxidoreductase, 2,5-DGK reductase, sorbitol dehydrogenase, mailc enzyme, or the like, as well as NAD(P)H:quinone oxidoreductase.

Example 8

Method of Indirectly Quantifying Microbe and Measuring Environmental Contamination by Measuring NADPH Concentration in Sample (1) Method of Analyzing NADPH in Cell to Indirectly Quantifying Cell Mass In the case in which cells are present in various environmental and NADPH, which is a biological activity marker, is essentially present therein. The reason is that in the case in which cells are not present or died, an amount of NADPH to be measured is lower than a basal level.

Therefore, the present inventors designed a method of utilizing his-mBFP capable of determining presence of microbe or confirmation of a contamination degree in almost real time, which was performed through processes of diluting a sample, spreading on a solid medium, observing the number of bacteria, and inversely operating a dilution ratio to calculate the total number of bacteria in the existing method.

More specifically, an ecological and environmental sample (soil, seawater, fresh water, or the like) or a specimen (necessities that may be easily contaminated, or the like) was extracted in a sterile container by aseptic technique to thereby be rapidly frozen or be maintained in a cold storage state, and then an experiment was conducted within a short time (in the case of the cold storage, within 1 hour).

A specimen that is dried and is not degenerated or rotted such as cereal flour, dry milk was not necessarily delivered in a frozen state, but sealed or closed in order to prevent secondary contamination. In the case in which a specimen was ice or ice cakes, the specimen was put into a sterile glass container and melted, and then the melted specimen was treated by the same method as that in the case of a liquid sample. It needs to be noted that when the sample is cold-stored for 1 day or more, an increase of psychrophilic bacteria, death of mesophilic bacteria and thermophilic bacteria may be caused. In the case of using ice for cooling, ice or melted ice water should not be directly contacted with the sample in order to prevent secondary contamination.

Devices for extracting the sample were dry-heated and flame-sterilized in advance, and different device was used for each sample.

The variously prepared ecological and environmental samples, specimens, or the like, were appropriately diluted with sterilized water using the aseptic technique, and then disruption was induced by a homogenizer for 2 to 10 minutes.

As a more specific preparation example of a test solution, there are a liquid specimen (substance in which extracted specimen was strongly agitated and mixed), a semi-fluidized specimen (obtained by well-mixing the extracted specimen using a sterilized glass rod, a sterilized spoon, or the like, mixing a predetermined amount of mixture with sterile normal saline again to be homogenized, and then recovering the supernatant), a solid specimen (obtained by cutting a predetermined amount of extracted specimen, adding sterile normal saline thereto, grinding the mixture using a homogenizer, and then recovering the supernatant), a powdery specimen (obtained by well mixing the specimen using the sterilized glass rod and spoon, mixing a predetermined mixture with sterile normal saline again to be homogenized, and then separating the supernatant), butter and oils (obtained by dissolving the specimen in a hot water bath at 65° C. or less within 15 minutes, adding sterile normal saline, homogenizing the mixture, and then extracting the supernatant), or the like, but the present invention is not limited thereto.

It could be confirmed that after the supernatants of the prepared sample was diluted as needed, and his-mBFP (1 to 5 μM) was added, fluorescence values were immediately measured to quantify the amount of NADPH present in the samples, and this quantified amount was divided by the content of NADPH in the microbe as a typical contamination source, such that a degree of relative contamination may be easily determined.

As the contamination source, there are various species, but in the case of microbes, since a concentration derivation between microbial species is not large, standard curves or verification tables for all of the species are not required. Through the above-mentioned result, it could be confirmed that with the detection method using his-mBFP according to the present invention, the degree of contamination by microbes may be determined in almost real time, and the detection method has relatively advantageous as compared to the existing plate culture method or microscopy. Particularly, it was certified that the detection method is a method capable of basically solving the deviation generated due to natural oxidation of NADPH caused by the pre/post treatment of the sample or secondary contamination problem.

(2) Method of Measuring Contamination Using NADPH of Microbe Cultured After Sample Containing Latent Contamination Material is Added Various organic materials, salts, or the like, pre-existing in samples are recognized as potential contamination materials since these materials may be used as nutrients of various living thing, particularly, microbes. In order to control eutrophication or food spoilage/purification, or the like, due to these contamination sources, these potential contamination materials should be determined based on a clear indicator. A test method capable of providing a basis of this determination using his-mBFP was designed.

More specifically, at the time of culture microbes using the same method as that in Example 2, a minimal medium (C and N-sources was lacked) was used, and a predetermined amount of sample (drinking water, fresh water, sea water, food, necessities, soil, or the like) was added. Then, culture was conducted enough to induce cell growth (for 1 to 2 days). A culture condition was the same as that in Example 2 so that it was advantageous to growth of mesophilic bacteria such as E. coli. During a culturing process, a predetermined amount of culture solution was recovered and treated by the above-mentioned method, and then a changed amount of NADPH concentration according to the passage of time was monitored. Presence or absence of an organic material/salt that may become a potential contamination material was determined based on the measured value.

In the case in which E. coli transformed with the recombinant vector pQE-mBFP according to the present invention is used in this process, whether or not the microbe grows may be confirmed only by measurement of fluorescence of the culture solution itself without using the above-mentioned process.

Figure 14:
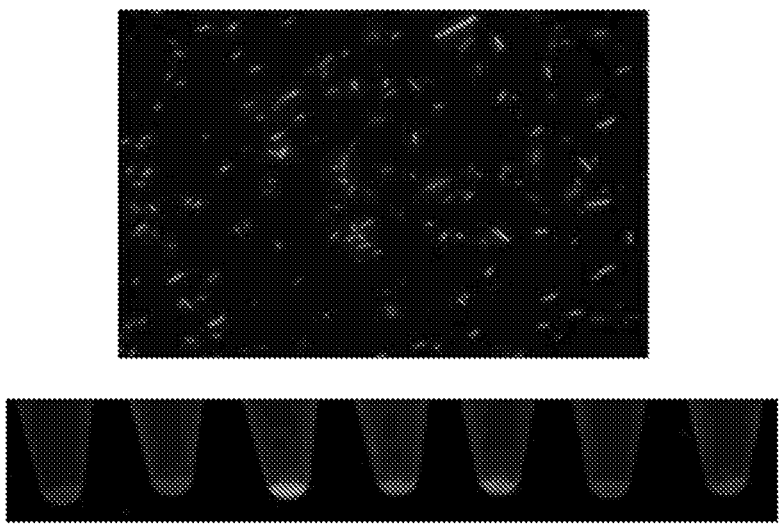
FIG. 14 is fluorescent images of a cell including his-mBFP of the present invention, wherein his-mBFP is over-expressed by growth induced due to latent contamination materials (organism/salts, or the like).

That is, as shown in FIG. 14, it could be confirmed that contamination materials existing in the medium are used as nutrients to induce growth of recombinant strains, such that an expressed amount of protein of cytoplasm is increased, thereby significantly increasing the fluorescence intensity. In this process, a degree of contamination of the sample may be measured by any one method of measuring the fluorescence value of the cell itself or recovering and then disrupting the cell to measure fluorescence value of a supernatant.

Example 9

Method of Selecting NADPH Dependent Enzyme (Dehydrogenase And Oxidoreductase) from Library Metagenome in an environmental sample was extracted using a genomic DNA isolation kit (promega) and partially cut using restriction enzyme BamH1 or Sau3A1 recognizing GATC to cut GATC. A library was constructed by a method of introducing the cut DNA fragments into a typical cloning vector (pBluscript IISK) to introduce the vector into E. coli host (BL21).

As a method for transformation, an electrophoration method was used according to a typical process. Hosts having the prepared library were spread on LB solid medium containing 50 μg/ml of ampicillin and cultured at 37° C. for 16 hours, and then each of the colonies was moved to a 96 well plate containing 350 μl of medium having the same composition and shaking-cultured for a predetermined time (24 to 48 hours) under the same condition. After culture, the cells were disrupted by treatment of cell lysis solution (containing 0.1% SDS or 1% triton X-100 and 0.5% lysozyme).

A substrate (1 to 5 mM), which is a target to be screened, and NADPH (1 mM) were added to the cell disrupted solution to induce a reaction. A changed amount of NADP(H) was calculated by adding his-mBFP (1 to 5 μM) to measuring fluorescence after the reaction for 10 to 60 minutes. Here, the reaction solution was diluted in consideration of a reaction mole ratio with his-mBFP.

Samples in which a residual NADPH content was changed by ±15% as compared to E. coli in other plates were selected from results obtained by quantifying NADP(H). After plasmid is isolated from the selected strain (plasmid DNA isolation kit, promega), presence or absence of the gene, which is a selecting target, was confirmed through sequence analysis, and as a result, a positive clone may be selected at a rate of 93% or more.

The present invention includes a suitable vector that may be used to prepare a library vector, a selectable marker, a host cell, a method for delivery into host cell, and the like, but is not limited thereto.

In addition, the present invention may selectively select an activity inhibitor by restricting the library in the above-mentioned process with a clone having an oxidation/reduction enzyme family, adding a specific compound as well as a substrate in a process of measuring the activities of these enzymes, calculating a changed amount of NADP(H) to compare the calculated value with that of a control group (only substrate was add). These processes mean that after clones having related enzyme activities are cultured and a substrate and NADP(H) are added thereto, a changed amount of NADPH is quantified while inducing a reaction in an environment in which various synthetic materials are present.

In more detail, compounds having a possibility as the activity inhibitor were added to reaction solution of NADPH dependent oxidoreductase as in Example 7 at each concentration (0.1 to 10 mM). While the reaction was carried out, a produced amount of NADPH according to addition of each compound was quantified, and an inhibition degree of specific enzyme activity was confirmed by comparing the produced amount of NADPH in the case of adding the compound (test group) with that of in the case of not adding (control group).

After rates of NADPH production (reduction) reaction according to the concentration changes of primary selected compounds were measured, $IC_{50}$ of each compound was calculated using a sigma plot program. The calculated results were shown in the following Table 3.

TABLE 3

| Enzyme | Inhibitor | $IC_{50}(\mu M)$ |
| --- | --- | --- |
| Alcohol dehydrogenase | Mulberroside A | 48.86 ± 4.9 |
| | Rhaponticin | 61.23 ± 4.1 |
| | Formepizole | 40.62 ± 5.8 |
| Isocitrate dehydrogenase | oxalomalic acid | 63.33 ± 5.2 |
| | methylisocitric acid | 101.75 ± 7.4 |
| Glucose-6-phosphate dehydrogenase | gallocatechin gallate | 225.37 ± 28.6 |
| | epicatechin gallate | 235.22 ± 37.8 |

As seen Table 3, the detection method using his-mBFP according to the present invention has advantages in that the inhibitor of NADPH dependent oxidoreductase (anti-microbial agent) may be efficiently selected and the method may be widely used in various quantifications, probes, diagnosis fields such as various kits for detecting physiological activity.

Since this Example was designed in order to evaluate reliability of the present invention, the case in which the activity inhibitor was included was described in the Example, but the present invention is not limited thereto.

Example 10

Recovery of NADPH from Biological Sample or Synthetic Sample Using his-mBFP Affinity (1) Preparation of his-mBFP Column Using Immobilized-Metal Affinity Chromatography (IMAC)

A column for NADPH separation/recovery was prepared by binding his-mBFP to an affinity chromatography. To this end, a Chelating Sepharose Fast Flow (BioProcess™) resin was sufficiently washed with 50 ml of a binding buffer (50 mM phosphate buffer, pH 7.4, 200 mM NaCl). When the Chelating Sepharose resin reached equilibrium, the binding buffer added with metal ions (($Cu^{2+}$, $Zn^{2+}$, $Ni^{2+}$, or $Co^{2+}$) were flowed at a flow rate of 2 ml/min to induce attachment, and then 100 ml of the binding buffer was flowed at a flow rate of 4 ml/min, thereby removing ions not bound to the column.

Next, the prepared resin was washed with 50 ml of mBFP binding buffer (20 mM Tris-HCl, pH 7.5) at a flow rate of 2 ml/min so as to reach equilibrium. When the resin reached equilibrium, mBPF binding buffer (20 mM Tris-HCl, pH 7.5) to which his-mBFP (10 mg) was added was flowed at a flow rate of 2 ml/min, thereby inducing attachment of protein. After 100 ml of mBFP binding buffer was flowed at a flow rate of 4 ml/min to remove protein not bound to the column, a NADPH affinity column (his-mBFP attached Chelating Sepharose column) was prepared.

(2) Recovery of NADPH Using his-mBFP Immobilized Column

In order to recover NADPH contained in a sample using the NADPH affinity column prepared in (1), a supernatant of the sample containing NADPH was prepared by the same method as in Example 6.

Here, in order to prevent loss of NADPH due to non-specific oxidation in a binding/elution process, the buffer was treated with a reducing agent, or residual oxygen was flushed with nitrogen ($N_2$ gas was introduced in to the buffer for 5 minutes). The prepared NADPH affinity column was sufficiently washed with buffer (50 ml, 20 mM Tris-HCl, pH 7.5) treated as described above so as to reach equilibrium. After the column reached equilibrium, the sample containing NADPH was flowed at a flow rate of 2 ml/min to induce attachment of NADPH, and then 100 ml of washing buffer (20 mM Tris-HCl, pH 7.5, 10 mM NaCl) was flowed at a flow rate of 4 ml/min to completely remove impurities not bound to the column. An elution buffer (20 mM Tris-HCl, 2 M NaCl, pH 7.5) was flowed to the prepared resin at the same flow rate to recover NADPH bound to his-mBFP.

In this case, all of the solutions flowed in each of the processes were recovered, and presence or absence and degree of absorption of NADPH were confirmed. In addition, an amount of NADPH recovered through the NADPH affinity column was measured by the same method as that in Example 3.

As a result, NADPH measured in *E. coli*, or plant tissue, (beans, or the like) was stably recovered at a level of about 70 to 85%. Although the case in which the present invention includes a method of using the immobilized column in which IMAC resin is attached to his-mBFP is described in Example 10, his-mBFP may be similarly coupled to a cibacron resin, and the present invention is not limited thereto.

SEQUENCE LIST TEXT

SEQ ID NO: 1: mBFP amino acid sequence
SEQ ID NO: 2: mBFP base sequence
SEQ ID NO: 3: his-mBFP amino acid sequence
SEQ ID NO: 4: his-mBFP base sequence
SEQ ID NO: 5: primier
SEQ ID NO: 6: primier

The invention claimed is:

1. A detection method of NADP(H) from the change of a fluorescence intensity by a reaction between [i] histidine-tagged metagenome-derived blue fluorescent protein (his-mBFP) having at least 95% sequence identity to the amino acid sequence of SEQ ID NO: 3, and [ii] NADPH, wherein said histidine-tagged metagenome-derived blue fluorescent protein is capable of emitting a fluorescence at a wavelength of about 450 nm.

2. The method of claim 1, wherein a concentration of NADP(H) existing in a sample is measured from the fluorescence intensity.

3. The method of claim 1, wherein an activity of NADP(H) dependent enzyme using NADP(H) as a coenzyme is measured from the fluorescence intensity.

4. The method of claim 3, wherein the NADP(H) dependent enzyme is NADP(H) dependent dehydrogenase or oxidoreductase.

5. The method of claim 1, wherein a detergent is further added and mixed at the time of the reaction of sample and mBFP.

6. The method of claim 5, wherein the detergent is at least one selected from the group of consisting of sodium dodecylsulfate, Na-deoxycholate, cetyltrimethylammonium bromide, dodecyl ethyl dimethyl-ammonium bromide, and 3-[(3-cholamidopropyl)dimethylammonio]-1-propane sulfonate.

* * * * *